(12) United States Patent
Didar et al.

(10) Patent No.: US 12,343,452 B2
(45) Date of Patent: Jul. 1, 2025

(54) FLUOROSILINATED LIQUID-INFUSED SURFACES WITH EMBEDDED BIOMOLECULES, METHODS OF MAKING AND USES THEREOF

(71) Applicant: McMaster University, Hamilton (CA)

(72) Inventors: Tohid F. Didar, Dundas (CA); Maryam Badv, Hamilton (CA); Zachary Cetinic, Toronto (CA); Amid Shakeri, Hamilton (CA)

(73) Assignee: McMaster University, Hamilton (CA)

( * ) Notice: Subject to any disclaimer, the term of this patent is extended or adjusted under 35 U.S.C. 154(b) by 1289 days.

(21) Appl. No.: 16/960,649

(22) PCT Filed: Jan. 9, 2019

(86) PCT No.: PCT/CA2019/050033
§ 371 (c)(1),
(2) Date: Jul. 8, 2020

(87) PCT Pub. No.: WO2019/136560
PCT Pub. Date: Jul. 18, 2019

(65) Prior Publication Data
US 2020/0330649 A1    Oct. 22, 2020

Related U.S. Application Data

(60) Provisional application No. 62/615,205, filed on Jan. 9, 2018.

(51) Int. Cl.
*A61L 27/54* (2006.01)
*A61K 47/69* (2017.01)
(Continued)

(52) U.S. Cl.
CPC .......... *A61L 27/54* (2013.01); *A61K 47/6901* (2017.08); *A61L 27/28* (2013.01);
(Continued)

(58) Field of Classification Search
CPC ... A61K 47/6901; A61L 31/048; A61L 31/08; B01J 19/0046; B01J 2219/00596;
(Continued)

(56) References Cited

U.S. PATENT DOCUMENTS 5,079,155 A   1/1992   Cox et al.
5,721,131 A   2/1998   Rudolph et al.
(Continued)

FOREIGN PATENT DOCUMENTS

WO    9205444 A1    4/1992
WO    9722631 A1    6/1997
(Continued)

OTHER PUBLICATIONS

K. Awsiuk, A. Bernasik, M. Kitsara, A. Budkowski, P. Petrou, S. Kakabakos, S. Prauzner-Bechcicki, J. Rysz, and I. Raptis, "Spectroscopic and microscopic characterization of biosensor surfaces with protein/amino-organosilane/silicon structure," Colloids Surfaces B Biointerfaces, vol. 90, No. 1, pp. 159-168, 2012.
(Continued)

*Primary Examiner* — Hai Y Zhang
(74) *Attorney, Agent, or Firm* — Smart & Biggar LP; Luba Naiberger

(57) ABSTRACT

The present application discloses biofunctional surfaces that have self-assembled monolayers of fluorine groups with "built-in" functional groups promote targeted cell and biomolecule binding to the surface while reducing non-specific binding. Further, this application also relates to methods for preparing functional biomolecules, viruses and cells that can be covalently immobilized to prepare biofunctional surfaces.

19 Claims, 20 Drawing Sheets

(51) Int. Cl.
A61L 27/28 (2006.01)
A61L 31/10 (2006.01)
A61L 31/16 (2006.01)
B01J 19/00 (2006.01)
C03C 17/30 (2006.01)

(52) U.S. Cl.
CPC .............. *A61L 31/10* (2013.01); *A61L 31/16* (2013.01); *B01J 19/0046* (2013.01); *C03C 17/30* (2013.01); *A61L 2400/18* (2013.01); *A61L 2420/06* (2013.01); *B01J 2219/00596* (2013.01); *B01J 2219/00637* (2013.01); *C03C 2218/31* (2013.01); *C03C 2218/33* (2013.01)

(58) Field of Classification Search
CPC .......... B01J 2219/00637; C07K 17/14; C07K 1/1077; C07K 16/00; C07K 16/2896; G01N 33/54393
See application file for complete search history.

(56) References Cited

U.S. PATENT DOCUMENTS

| | | | |
|---|---|---|---|
| 6,858,713 | B1 | 2/2005 | Bradley et al. |
| 6,979,728 | B2 | 12/2005 | Bradley et al. |
| 9,121,306 | B2 | 9/2015 | Aizenberg et al. |
| 9,121,307 | B2 | 9/2015 | Aizenberg et al. |
| 9,630,224 | B2 | 4/2017 | Aizenberg et al. |
| 9,932,484 | B2 | 4/2018 | Aizenberg et al. |
| 2015/0173883 | A1 | 6/2015 | Ingber et al. |
| 2017/0151546 | A1* | 6/2017 | Peck .................... B01J 19/0046 |

FOREIGN PATENT DOCUMENTS

| | | |
|---|---|---|
| WO | 2015054652 A2 | 4/2015 |
| WO | 2016118464 A2 | 7/2016 |
| WO | 2017095958 A1 | 6/2017 |
| WO | 2019136560 A1 | 7/2019 |

OTHER PUBLICATIONS

K. Awsiuk, A. Budkowski, A. Psarouli, P. Petrou, A. Bernasik, S. Kakabakos, J. Rysz, and I. Raptis, "Protein adsorption and covalent bonding to silicon nitride surfaces modified with organo-silanes: Comparison using AFM, angle-resolved XPS and multivariate ToF-SIMS analysis," Colloids Surfaces B Biointerfaces, vol. 110, pp. 217-224, 2013.
M. Badv, I. H. Jaffer, J. I. Weitz, and T. F. Didar, "An omniphobic lubricant-infused coating produced by chemical vapor deposition of hydrophobic organosilanes attenuates clotting on catheter surfaces," Sci. Rep., vol. 7, No. 1, p. 11639, 2017.
Badv et al., Lubricant-Infused Surfaces with Built-In Functional Biomolecules Exhibit Simultaneous Repellency and Tunable Cell Adhesion, ACS Nano, Nov. 27, 2018, pp. 10890-10902, Abstract.
D. G. Castner and B. D. Ratner, Biomedical surface science: Foundations to frontiers, vol. 500, No. 1-3. 2002.
H. H. Chien, K. J. Ma, C. H. Kuo, and S. W. Huang, "Effects of plasma power and reaction gases on the surface properties of ePTFE materials during a plasma modification process," Surf. Coatings Technol., vol. 228, No. Suppl. 1, pp. S477-S481, 2013.
P. Filippini, G. Rainaldi, A. Ferrante, B. Mecheri, G. Gabrielli, M. Bombace, P. L. Indovina, and M. T. Santini, "Modulation of osteosarcoma cell growth and differentiation by silane-modified surfaces," J. Biomed. Mater. Res., vol. 55, No. 3, pp. 338-349, 2001.
J. E. Gautrot, W. T. S. Huck, M. Welch, and M. Ramstedt, "Protein-resistant NTA-functionalized polymer brushes for selective and stable immobilization of histidine-tagged proteins," ACS Appl. Mater. Interfaces, vol. 2, No. 1, pp. 193-202, 2010.
C. Haensch, S. Hoeppener, and U. S. Schubert, "Chemical modification of self-assembled silane based monolayers by surface reactions," Chem. Soc. Rev., vol. 39, No. 6, p. 2323, 2010.
J. M. Harris and R. B. Chess, "Effect of pegylation on pharmaceuticals.," Nat. Rev. Drug Discov., vol. 2, No. 3, pp. 214-221, 2003.
C. Howell, T. L. Vu, C. P. Johnson, X. Hou, O. Ahanotu, J. Alvarenga, D. C. Leslie, O. Uzun, A. Waterhouse, P. Kim, M. Super, M. Aizenberg, D. E. Ingber, and J. Aizenberg, "Stability of surface-immobilized lubricant interfaces under low," Chem. Mater., vol. 27, No. 5, pp. 1792-1800, 2015.
International Search Report and Written Opinion of corresponding International Application No. PCT/CA2019/050033 dated May 1, 2019, 15 pages.
L. S. Jang and H. J. Liu, "Fabrication of protein chips based on 3-aminopropyltriethoxysilane as a monolayer," Biomed. Microdevices, vol. 11, No. 2, pp. 331-338, 2009.
J. Kim, J. Cho, P. M. Seidler, N. E. Kurland, and V. K. Yadavalli, "Investigations of chemical modifications of amino-terminated organic films on silicon substrates and controlled protein immobilization," Langmuir, vol. 26, No. 4, pp. 2599-2608, 2010.
D. J. Kim, J. M. Lee, J. G. Park, and B. G. Chung, "A self-assembled monolayer-based micropatterned array for controlling cell adhesion and protein adsorption," Biotechnol. Bioeng., vol. 108, No. 5, pp. 1194-1202, 2011.
D. C. Leslie, A. Waterhouse, J. B. Berthet, T. M. Valentin, A. L. Watters, A. Jain, P. Kim, B. D. Hatton, A. Nedder, K. Donovan, E. H. Super, C. Howell, C. P. Johnson, T. L. Vu, D. E. Bolgen, S. Rifai, A. R. Hansen, M. Aizenberg, M. Super, J. Aizenberg, and D. E. Ingber, "A bioinspired omniphobic surface coating on medical devices prevents thrombosis and biofouling.," Nat. Biotechnol., vol. 32, No. 11, pp. 1134-1140, 2014.
Q. L. Li, N. Huang, C. Chen, J. L. Chen, K. Q. Xiong, J. Y. Chen, T. X. You, J. Jin, and X. Liang, "Oriented immobilization of anti-CD34 antibody on titanium surface for self-endothelialization induction," J. Biomed. Mater. Res.—Part A, vol. 94, No. 4, pp. 1283-1293, 2010.
Y. Liu and J. Yu, "Oriented immobilization of proteins on solid supports for use in biosensors and biochips: a review," Microchim. Acta, vol. 183, No. 1, pp. 1-19, 2016.
C. Y. K. Lung and J. P. Matinlinna, "Aspects of silane coupling agents and surface conditioning in dentistry: An overview," Dent. Mater., vol. 28, No. 5, pp. 467-477, 2012.
S. P. Pujari, L. Scheres, A. T. M. Marcelis, and H. Zuilhof, "Covalent surface modification of oxide surfaces," Angew. Chemie—Int. Ed., vol. 53, No. 25, pp. 6322-6356, 2014.
R. R. Ravindranath, A. Romaschin, and M. Thompson, "In vitro and in vivo cell-capture strategies using cardiac stent technology—A review," Clin. Biochem., vol. 49, No. 1, pp. 186-191, 2016.
F. Rusmini, Z. Zhong, and J. Feijen, "Protein immobilization strategies for protein biochips," Biomacromolecules, vol. 8, No. 6, pp. 1775-1789, 2007.
R. S. Smith, Z. Zhang, M. Bouchard, J. Li, H. S. Lapp, G. R. Brotske, D. L. Lucchino, D. Weaver, L. A. Roth, A. Coury, J. Biggerstaff, S. Sukavaneshvar, R. Langer, and C. Loose, "Vascular Catheters with a Nonleaching Poly-Sulfobetaine Surface Modification Reduce Thrombus Formation and Microbial Attachment," Sci. Transl. Med., vol. 4, No. 153, p. 153ra132-153ra132, 2012.
I. Sotiri, J. C. Overton, A. Waterhouse, and C. Howell, "Immobilized liquid layers: a new approach to anti-adhesion surface for medical applications.," Exp. Biol. Med., vol. in press, pp. 1-10, 2016.
A. Tan, D. Goh, Y. Farhatnia, N. G, J. Lim, S. H. Teoh, J. Rajadas, M. S. Alavijeh, and A. M. Seifalian, "An Anti-CD34 Antibody-Functionalized Clinical-Grade POSS-PCU Nanocomposite Polymer for Cardiovascular Stent Coating Applications: A Preliminary Assessment of Endothelial Progenitor Cell Capture and Hemocompatibility," PLoS One, vol. 8, No. 10, pp. 1-14, 2013.
T.-S. Wong, S. H. Kang, S. K. Y. Tang, E. J. Smythe, B. D. Hatton, A. Grinthal, and J. Aizenberg, "Bioinspired self-repairing slippery surfaces with pressure-stable omniphobicity.," Nature, vol. 477, No. 7365, pp. 443-447, 2011.
F. Yang, S.-C. Feng, X.-J. Pang, W.-X. Li, Y.-H. Bi, Q. Zhao, S.-X. Zhang, Y. Wang, and B. Feng, "Combination coating of chitosan and anti-CD34 antibody applied on sirolimus-eluting stents can promote endothelialization while reducing neointimal formation," BMC Cardiovasc. Disord., vol. 12, No. 1, p. 96, 2012.

(56) References Cited

OTHER PUBLICATIONS

M. Yin, Y. Yuan, C. Liu, and J. Wang, "Combinatorial coating of adhesive polypeptide and anti-CD34 antibody for Improved endothelial cell adhesion and proliferation," J. Mater. Sci. Mater. Med., vol. 20, No. 7, pp. 1513-1523, 2009.

* cited by examiner a)

b)

a)

b)

FLUOROSILINATED LIQUID-INFUSED SURFACES WITH EMBEDDED BIOMOLECULES, METHODS OF MAKING AND USES THEREOF

CROSS-REFERENCE TO RELATED APPLICATIONS

This application is National Stage of International Application No. PCT/CA2019/050033 filed on Jan. 9, 2019 which claims the benefit of priority from U.S. Provisional Patent Application Ser. No. 62/615,218 filed on Jan. 9, 2018, and U.S. Provisional Patent Application Ser. No. 62/615,205 filed on Jan. 9, 2018, the contents of both of which are incorporated herein by reference in their entirety.

FIELD

The present application relates to methods of creating biofunctional surfaces. More specifically the present application relates to surfaces that have self-assembled monolayers of fluorine groups with "built-in" functional groups that promote targeted cell and biomolecule binding to the surface while reducing non-specific binding. Further, this application also relates to methods for preparing functional biomolecules, viruses and cells that can be covalently immobilized to prepare biofunctional surfaces.

INTRODUCTION

Smart bio-functional surfaces have been widely investigated in recent years due to their numerous applications in bioengineering including biosensors, medical implants, medical diagnostics and therapeutics [1]. Optimum performance for such biofunctional surfaces on which biomolecules are immobilized is important, and requires both targeted binding of desired biomolecules and prevention of non-specific adhesion of biomarkers and cells [2], [3]. Therefore, designing smart biofunctional surfaces that both prevent non-specific adhesion and promote desired functionality is of great importance. Development of modified surfaces for targeted binding using self-assembled monolayers (SAMs) of coupling agents such as silanes, has widely been investigated and studied for covalent attachment of biomaterials and biomolecules and they have shown to be promising candidates for producing biofunctional surfaces [4]. In addition to biofunctionality, one of the key characteristics that biofunctional surfaces are required to have is reduced non-specific binding of biomolecules and as a result a higher sensitivity and selectivity [1]. Many developments have been made to better incorporate this functionality into the bioengineered surfaces. Bovine serum albumin (BSA) has been widely used as a blocking agent in biofunctional surfaces [5]-[10]. However, BSA cannot reduce biofilm formation and since BSA is not covalently immobilized on surfaces, the stability of this blocking agent is low and can be removed by extensive washing [2]. Poly(ethylene glycol) (PEG) is also well know hydrophilic polymer that has been used extensively for reducing nonspecific protein adsorption [9], [11], [12]. However, the non-stability and the degradation rate of PEG makes this polymer less suitable for long-term applications [3].

As noted above, the sensitivity of biosensors relies on reducing background signal resulting from non-specific binding of biomolecules, as well as, on producing an irreversible and stable specific biomolecule binding to the surface [13], [14]. Several techniques and methods have been proposed for the immobilization of biomolecules on different surfaces, such as physical and non-covalent adsorption [15] or covalent attachment via amine or carboxyl moieties [16]-[18] which all require intensive modification of the initial surface, in order to prepare a suitable and active interface for biomolecule immobilization [19]. These techniques usually lead to random orientation of the biomolecule on the modified surface, resulting in decreased binding affinity and low density of functional binding sites and also low stability under flow conditions [19].

More recently, omniphobic lubricant infused coatings have been developed based on tethering biocompatible liquid lubricants on self-assembled monolayers (SAMs) of hydrophobic organosilanes [20], [21] such as amino-silanes (e.g. (3-Aminopropyl) triethoxysilane, (APTES)) [14], [22]-[26] on the initial surface, and utilizing the amine ($NH_2$) terminal for covalent bonding of biomolecules [25]. These surfaces outperform a range of hydrophilic coatings [27] developed to resist protein adhesion. Furthermore, lubricant-infused omniphobic coatings have been more effective than PEG or albumin for blocking non-specific adhesion of cells and bacteria [28], [29]. In addition to increasing bio-compatibility, these surfaces are stable and durable when exposed to physiological shear stress in vitro [20], [30]. Therefore, lubricant-infused silanized surfaces represent a promising choice for bioengineered devices that have the potential to prevent non-specific adhesion of proteins and other biomolecules.

Creating SAMs could be done in both liquid or vapor phase [31]. One of the main limitations of this technique is the chemical modification and coating of the entire binding surface with the coupling agent and ultimately the change in the bulk surface properties of the initial surface. Although extensive research has been devoted to this area, creating uniform silane monolayers is still challenging and difficult to create [32]. In addition, since not all the coupling agent molecules present on the surface will be utilized for biomolecule attachment, these remaining sites can also act as active sites for protein and non-specific attachment of biomolecules in surfaces modified for biomedical applications. Previous efforts involved mixing two organosilanes (e.g. (3-Aminopropyl) triethoxysilane, (APTES) and trichloro (1H,1H,2H,2H-perfluorooctyl) silane (TPFS)) to create self-assembled monolayers of both silanes. This makes the process time consuming, more difficult to control and challenging to maintain both functionality and omniphobicity. Further, in existing published methods for covalent attachment of antibodies and proteins on surfaces, the substrate itself is first entirely coated with one or several coupling agents and/or chemical compounds or a combination of biomolecule and anchoring moieties.

United States patent application publication no. US2015/017383 describes a methods for modifying surfaces for simultaneous repellency and targeted binding of desired moieties by non-covalently immobilizing a lubricating layer over the surface of a substrate and incorporating binding groups that must extend over the surface of the lubricating layer or be retained within the lubricating layer. The binding groups have an affinity with a target moiety and are immobilized to the substrate via anchoring molecules.

There is a need to develop more efficient methods to obtain biosurfaces that integrate both important features of biofunctionality and repellency on one single substrate. There is equally a need to develop functionalized biomolecules, viruses and cells that can be efficiently attached to functionalized biosurfaces.

SUMMARY

A method of modifying substrates to incorporate fluorosilanes and reactive functional groups for attachment of biomolecules is disclosed herein. The resulting substrates, once treated with fluoro-lubricants, provide omniphobic biomolecule-modified surfaces that show reduced non-specific interactions. Such materials are useful for a number of applications, including for example, biosensors, medical implants, medical diagnostics and therapeutics.

In some embodiments, the present application describes a technique to generate surfaces that are both biofunctional and lubricant-infused and therefore capable of preventing or decreasing non-specific adhesion. In some embodiments, surfaces obtained from this technique comprise two main regions:

i. hydroxyl, carboxyl and/or amino functional moieties that are formed using a post fluorosilanization process (e.g. plasma treatment) and that can be used to couple functional moieties to the surface (e.g. silanes) for biospecies immobilization, or used for direct biospecies immobilization (e.g. via carboxyl or amino functional groups on the biospecies or via silanized biospecies); and ii. a fluorinated-lubricant infused area that highly inhibits non-specific binding and acts as a surface blocker.

It was surprisingly found that biospecies could be attached to the surface of the substrate (made accessible by etching the fluorosilanated surfaces) to provide a functionally active substrate without the need for the biospecies to extend over the surface of the lubricating layer or be retained within the lubricating layer as in US 2015/0173883.

Accordingly, in one aspect, the present application relates to a method for producing biofunctional fluorosilinated substrates comprising a. coating a surface of a substrate with a fluorosilane to create at least one fluorosilane monolayer on the surface to provide a fluorinate surface on the substrate wherein the substrate comprises surface hydroxyl groups or has been treated to form surface hydroxyl groups;

b. etching the fluorosilinated surface on the substrate to provide reactive functional groups on at least a portion of the fluorosilinated surface of the substrate; and c. attaching biomolecules to the reactive functional groups to obtain the biofunctional fluorosilinated substrates.

In some embodiments, before exposing the substrates to complex biological environments, the prepared biofunctional substrates are optionally coated with a fluorinated lubricant in order to add repellent properties to the surface.

In some embodiments, the present application also relates to biofunctional substrates prepared using methods of the present application.

In some embodiments, the methods or the biofunctional substrates of the present application do not require additional blocking steps using blocking agents (e.g. BSA, PEG), which is an additional step required after creating functionalized surfaces and as a result reduces the number steps needed for obtaining the product.

In some embodiments, the application includes a method of producing biofunctional fluorosilinated surfaces that have self-assembled monolayers of fluorine with built-in functional groups, comprising:

a. oxygen plasma treating the surface to induce hydroxyl groups b. coating the surface with a fluorinated monolayer c. generating functional groups on the surface created using plasma etching d. attaching biospecies to the functional groups created on fluorinated surfaces.

In one aspect, the present application also includes a method of producing silanzed biospecies such as biomolecules containing amine and carboxyl groups (e.g. antibodies and proteins), viruses as well as living cells, that allows the biospecies to be optionally, covalently attached to solid surfaces using silane binding chemistry. Accordingly, in some embodiments, the present application includes a method of producing a silanized biospecies comprising:

a. reacting a biospecies with a silane-containing molecule, wherein the silane containing molecule comprises a functional group that reacts with a complementary functional group on the biospecies and a silane functional group of the formula —$SiR^1R^2R^3$,
wherein one or more of $R^1$, $R^2$ and $R^3$ is OH or a group that is converted by hydrolysis to OH, and the remaining of $R^1$, $R^2$ and $R^3$ is selected from $C_{1-6}$alkyl,
and the biospecies and the silane-containing molecule are reacted under conditions to produce the silanized biospecies;

b. purifying the silanized biospecies under conditions to remove excess of the silane-containing molecule; and c. optionally producing a storage solution or powder of the purified silanized biospecies.

In some embodiments, the present application includes a method of preparing silanized biospecies through coupling the functional groups of a silane molecule to available functional groups on the biospecies (such as amine and carboxyl groups) comprising:

a. incubating the biospecies with a desired silane in a solution, b. purifying the resulting mixture to removing excess silane and c. producing a storage solution or a powder (i.e. lyophilized) of pure silanized biospecies wherein the resulting silanized biospecies has available free Si—OH moieties that can then be covalently attached to hydroxyl terminated surfaces.

Prior to immobilizing the biospecies on a surface of a substrate, the carboxyl groups (COOH) present on the biospecies itself can be targeted and modified with a silane-containing coupling agent (e.g. 3-aminopropyl-triethoxysilane-APTES), using for example the carbodiimide, amine-carboxyl or amine-epoxy cross-linker chemistry, and then the silanized biospecies can be immobilized on hydroxyl (OH) terminated surfaces.

In another aspect, the present application also relates to the process of purification of silanized biospecies prepared by a method of the present application comprising dialyzing a reaction mixture containing the functionalized biospecies to obtain a pure silanized biospecies solution and lyophilizing or freeze-drying the pure silanized biospecies solution to a powder.

In another aspect, the present application also relates to the silanized biospecies prepared by a method of the application.

In another aspect, the present application also relates to a method of functionalizing biosurfaces prepared by a method of the present application with the silanized biospecies prepared by a method of the present application, comprising contacting the hydroxyl or Si—OH groups on the biosurfaces with the silanized biospecies to create covalent attachments. In another aspect, the present application also relates to use of the silanized biospecies of the present application to functionalize biosurfaces.

In some embodiments, the methods of the present application could present the potential advantage of reducing the steps required to obtain a biofunctional surface compared to some existing techniques, and of reducing the need for chemically modifying the substrate with a coupling agent and/or other adhesive polymers or chemicals in order to covalently attach the biomolecule and as a result retaining the bulk surface properties of the modified surface significantly reducing the amount of non-reacted functional groups on the solid surface. Controlling the amount and concentration of protein or antibody attached to the surface by changing the concentration of the initial biomolecule solution is also an advantage of this technique compared to other available approaches, which can result in better preserving the innate properties of the substrate.

DRAWINGS

The embodiments of the application will now be described in greater detail with reference to the attached drawings in which:

FIG. 1 shows a schematic illustration of an exemplary method for preparing biofunctional fluorosilanized surfaces. Surfaces are initially coated with a fluorosilane molecule (e.g. using oxygen plasma activation followed by either chemical vapor deposition (CVD) or liquid phase deposition (LPD). Subsequently the coated surfaces are exposed to a plasma gas (e.g. oxygen ($O_2$) plasma treatment) in order to partially remove the fluorosilinated layer on the surface and add the functional groups (e.g. hydroxyl functional groups) to the substrate. In the next step, coupling agents such as an aminosilane (e.g. aminopropyltriethoxysilane (APTES)) are added to the surface and used to attach biomolecules on the surface. Further surface blocking is performed by incorporating an additional lubricant layer.

Figure 4:
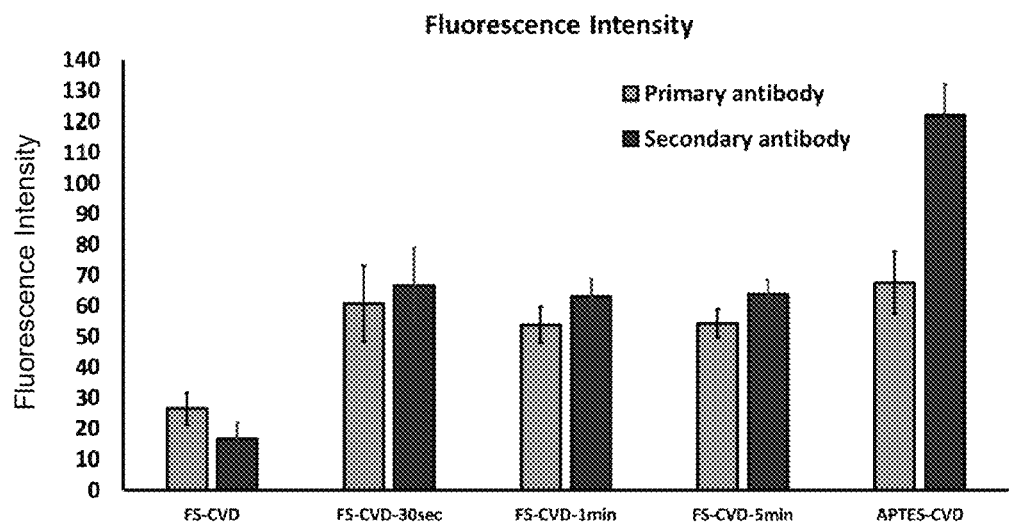
Figure 4:
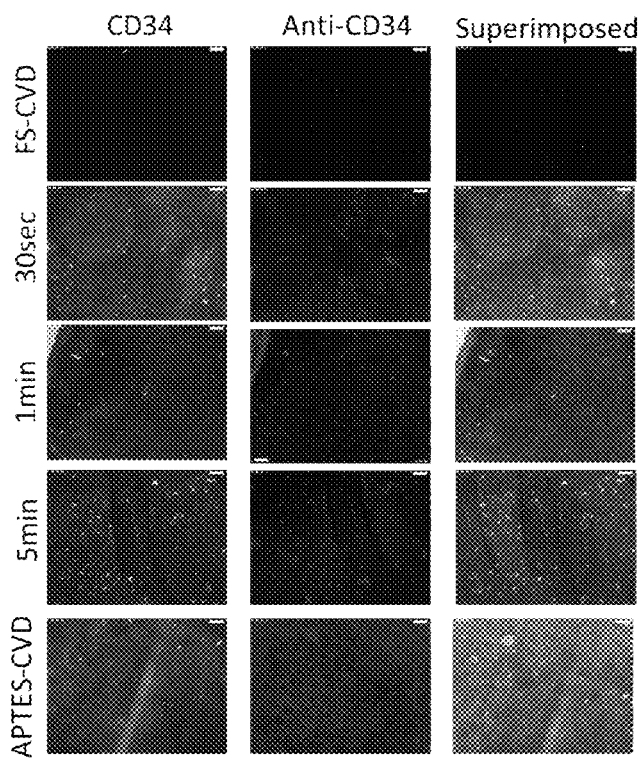

FIG. 4 shows fluorescence microscopy of exemplary plasma-treated fluorosilanized surfaces that have been modified with APTES and antiCD34 antibodies. A secondary antibody (goat anti-mouse IgG antibody modified with Alexa Fluor 594) was used for visualization. FIG. 4a shows the fluorescence intensities of primary and secondary antibodies attached to the exemplary fluorosilanized surfaces that have been plasma treated for different time periods. FIG. 4b, shows the representative fluorescence images of the exemplary surfaces treated with the primary (anti-CD34 antibody) and secondary (goat anti-mouse IgG antibody modified with Alexa Fluor 594) antibodies.

Figure 5:
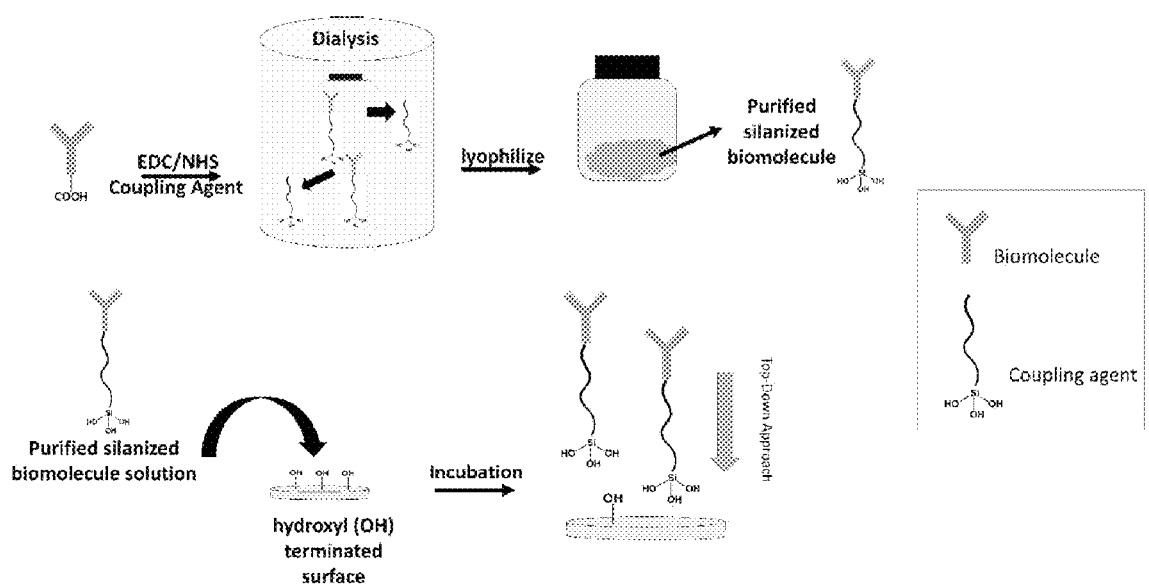

FIG. 5 shows a schematic illustration of an exemplary method of preparing silanized biospecies in which first the biospecies are chemically modified with a silane coupling agent, purified and then covalently attached to the active surface according to one embodiment of the present application.

Figure 6:
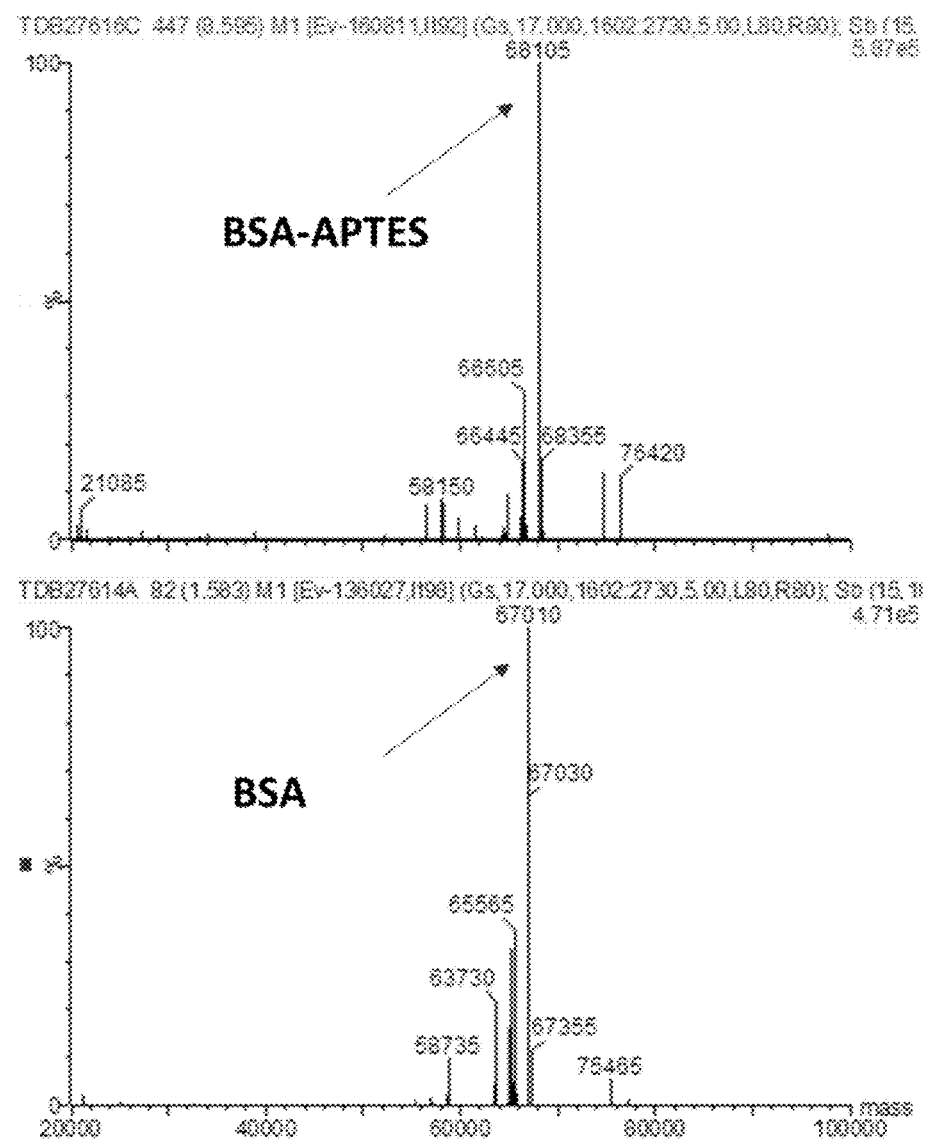

FIG. 6 shows the mass spectrometry results obtained from the non-modified BSA and BSA-APTES proteins.

Figure 7:
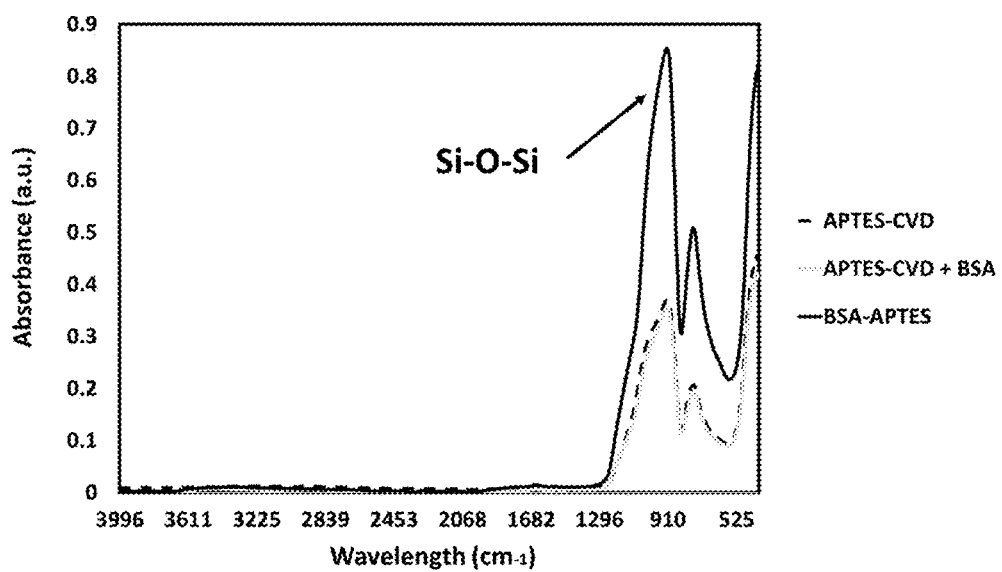

FIG. 7 shows the IR-FTIR results obtained from glass substrates modified with BSA-APTES and APTES-CVD.

Figure 8:
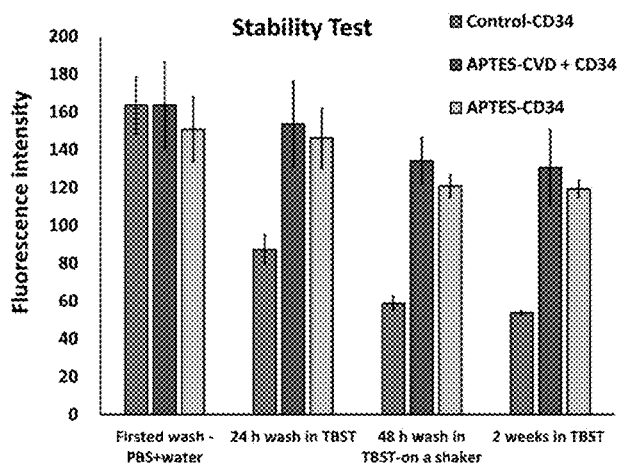
Figure 8:
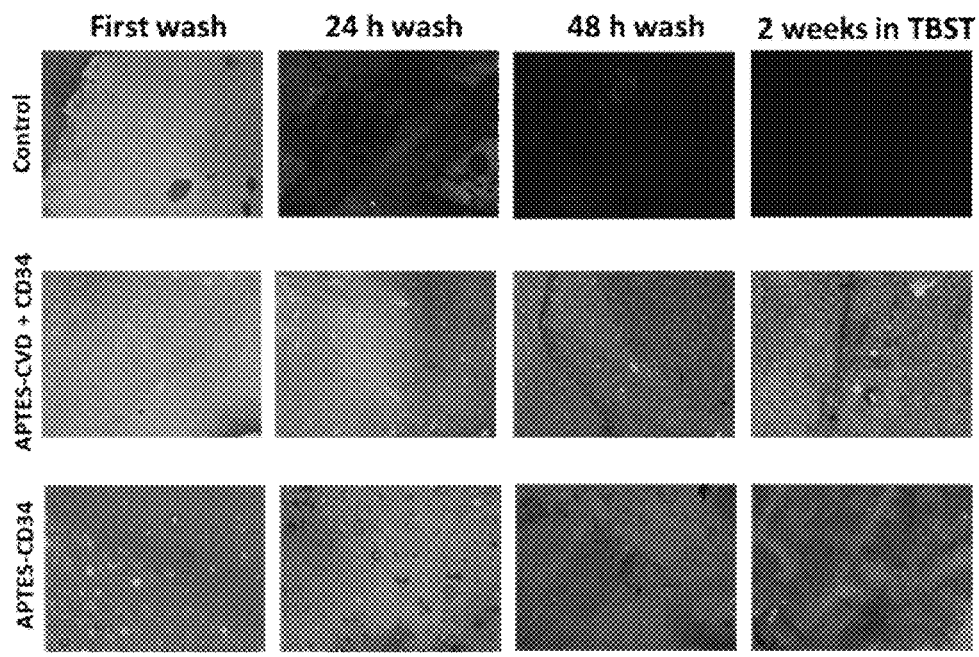

FIG. 8 shows the fluorescence intensity results obtained from the stability test performed on surfaces modified with exemplary CD34-APTES and APTES-CVD+CD34 compared with controls. FIG. 8a shows the fluorescence intensity of different treated surfaces after multiple washing steps. Surfaces were washed with 1% TBST and kept for up to 2 weeks in order to investigate the stability of the antibody treated surfaces. Surfaces functionalized using the conventional technique (chemical vapor deposition of APTES and then functionalization with anti-CD34 antibody) and physical adsorption of anti-CD34 antibody were used as control samples. FIG. 8b shows the representative fluorescence images of the antibody treated surfaces after each washing step.

Figure 9:
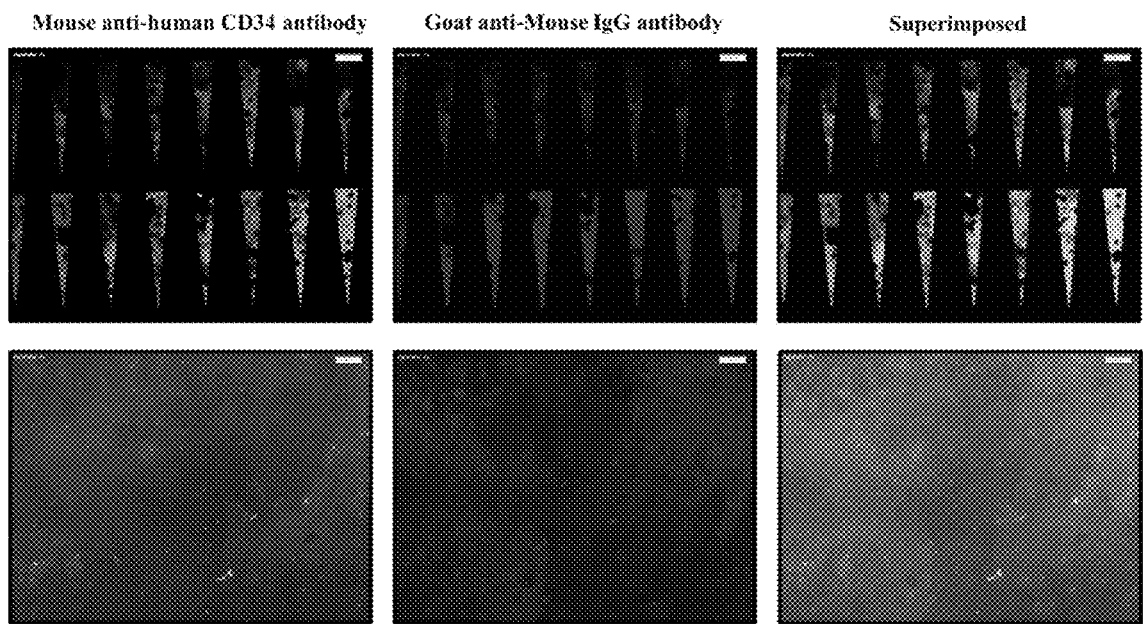

FIG. 9 shows the fluorescence images of a surface modified with an exemplary silanized antibody confirming that the modified antibody remains highly functional and successfully binds to the secondary antibody.

Figure 10:
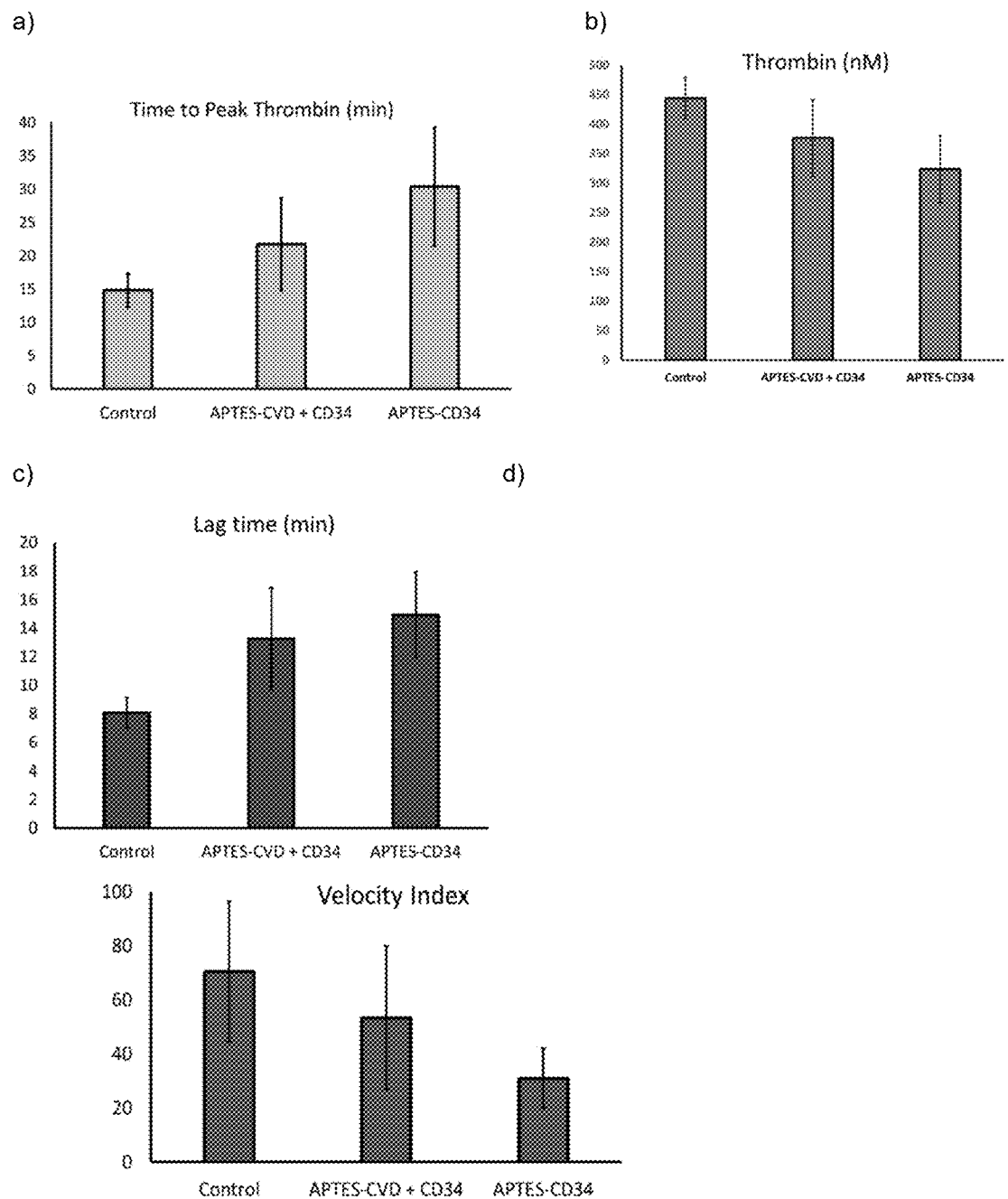

FIG. 10 shows the results obtained from the thrombin generation assay performed on polytetrafluoroethylene (PTFE) based surfaces modified with anti-CD34 antibody with both the conventional technique (chemical vapor deposition of APTES and immobilization of anti-CD34 using EDC/NHS chemistry) and the methods of the present application. Graphical results are presented for the amount of thrombin generated (nM), the time to peak thrombin (min), the lag time (min) and the velocity index (nM/min).

Figure 11:
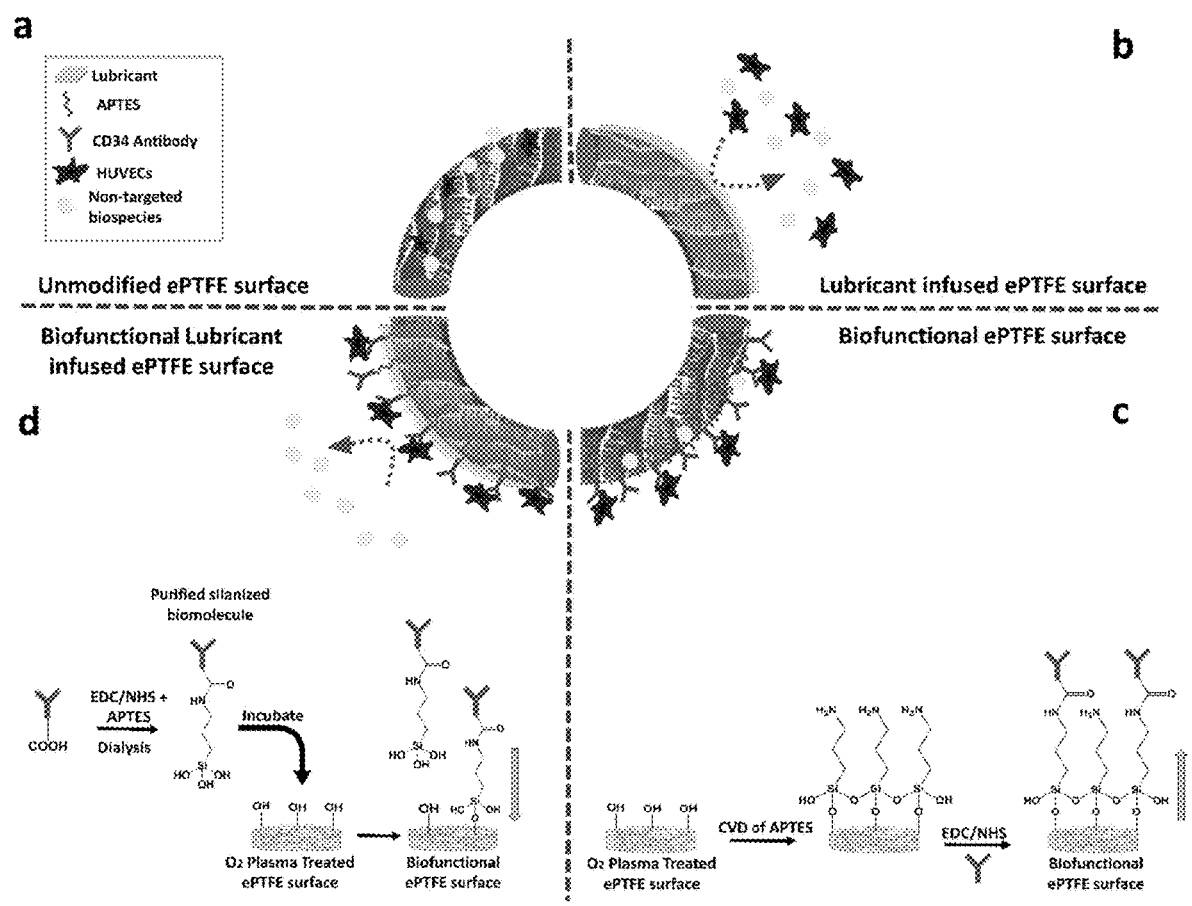

FIG. 11 shows a schematic representation of the different modification steps on the PTFE surface. a) Control ePTFE grafts. b) Lubricant-infused ePTFE grafts. c) Exemplary APTES-CVD treated surfaces biofunctionalized with anti-CD34 antibody. d) Biofunctional lubricant-infused ePTFE grafts.

Figure 12:
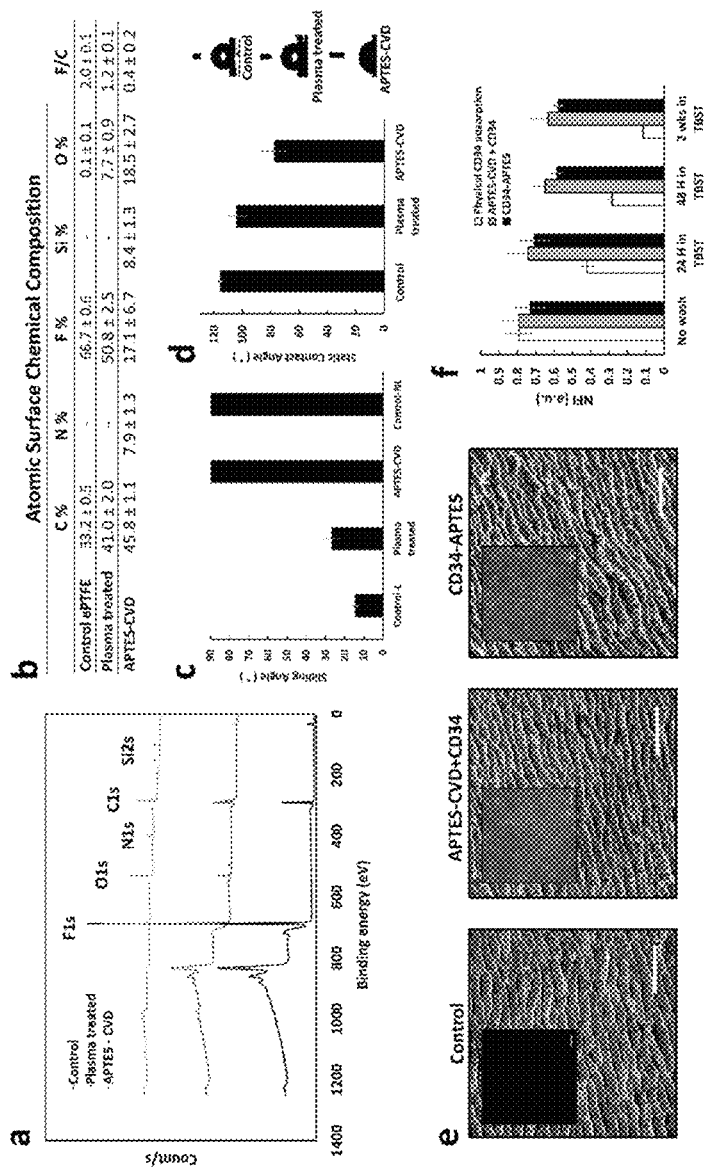

FIG. 12 shows the surface chemical composition and the slippery properties of the control and exemplary modified surfaces. a) A representative graph and b) the corresponding table of the surface atom % of different elements present on the ePTFE surfaces. c) Sliding angle and d) contact angle results of unmodified, oxygen plasma treated and APTES treated surfaces. e) Fluorescence microscopy and SEM was performed on anti-CD34 treated surfaces in order to confirm the binding of the antibody to the PTFE surfaces and to investigate the morphology of the surface after each modification step. f) The stability and covalent attachment of the CD34-APTES and APTES-CVD+CD34 was confirmed by incubating the treated surfaces in 1% TBST buffer up to 2 weeks.

Figure 13:
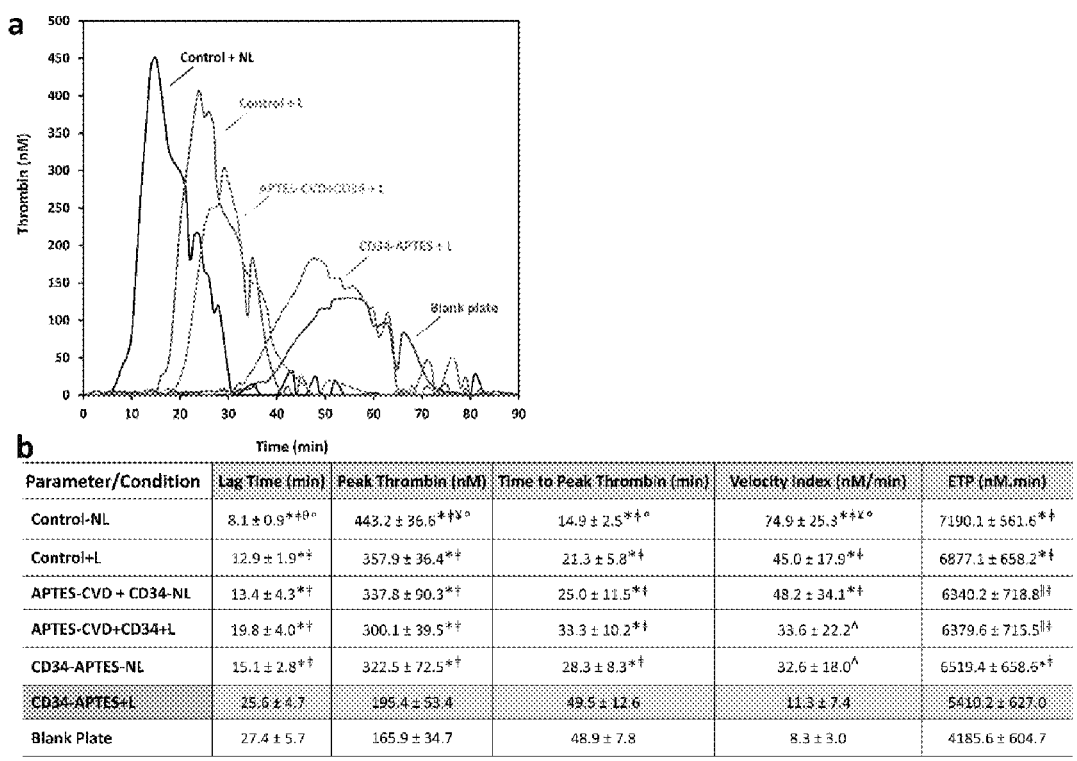

FIG. 13 shows the effect of different modification techniques on thrombin generation. a) A representative thrombin vs. time plot is shown. b) Thrombin generation parameters were determined in empty wells or wells containing control or exemplary modified PTFE surfaces. Values represent means±SD of at least 12 samples.

Figure 14:
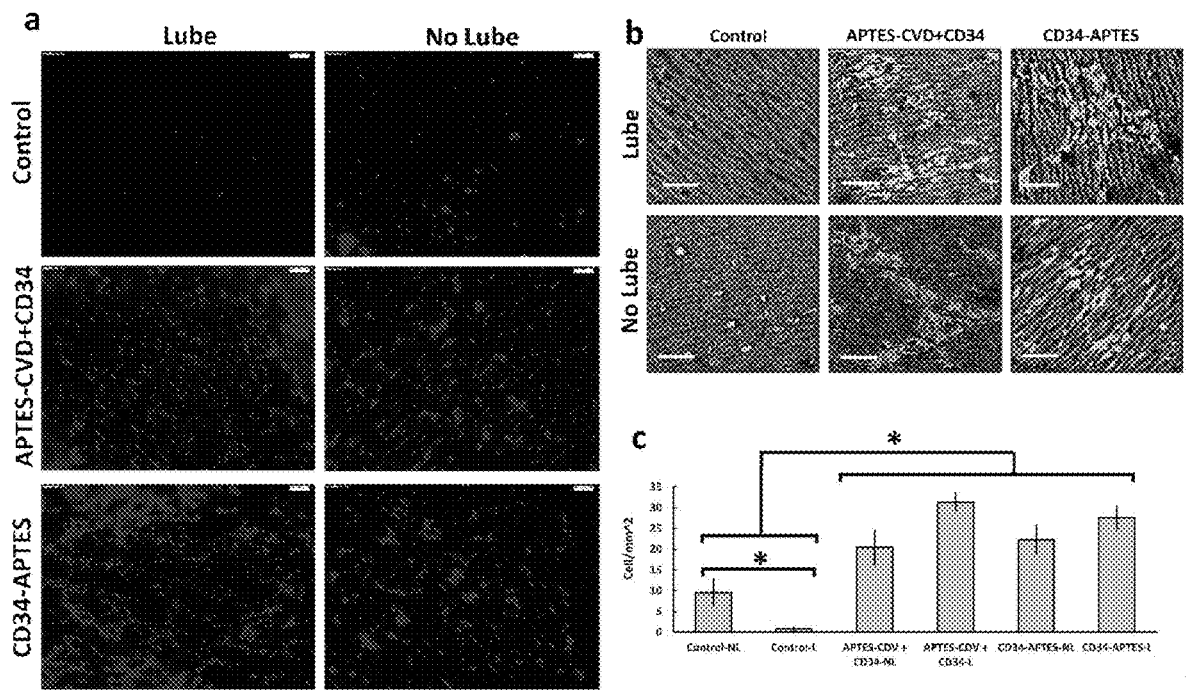

FIG. 14 shows short term endothelial cell adhesion on control and exemplary CD34 modified surfaces. a) Representative fluorescence images of the RFP-HUVECs adhered to the ePTFE samples. Treated and control surfaces were incubated with RFP-HUVECs for 24 hours and the cell adhesion and formation of the endothelial layer was investigated. b) SEM images of the cell treated ePTFE surfaces. c) Cell count per $mm^2$ of surfaces.

Figure 15:
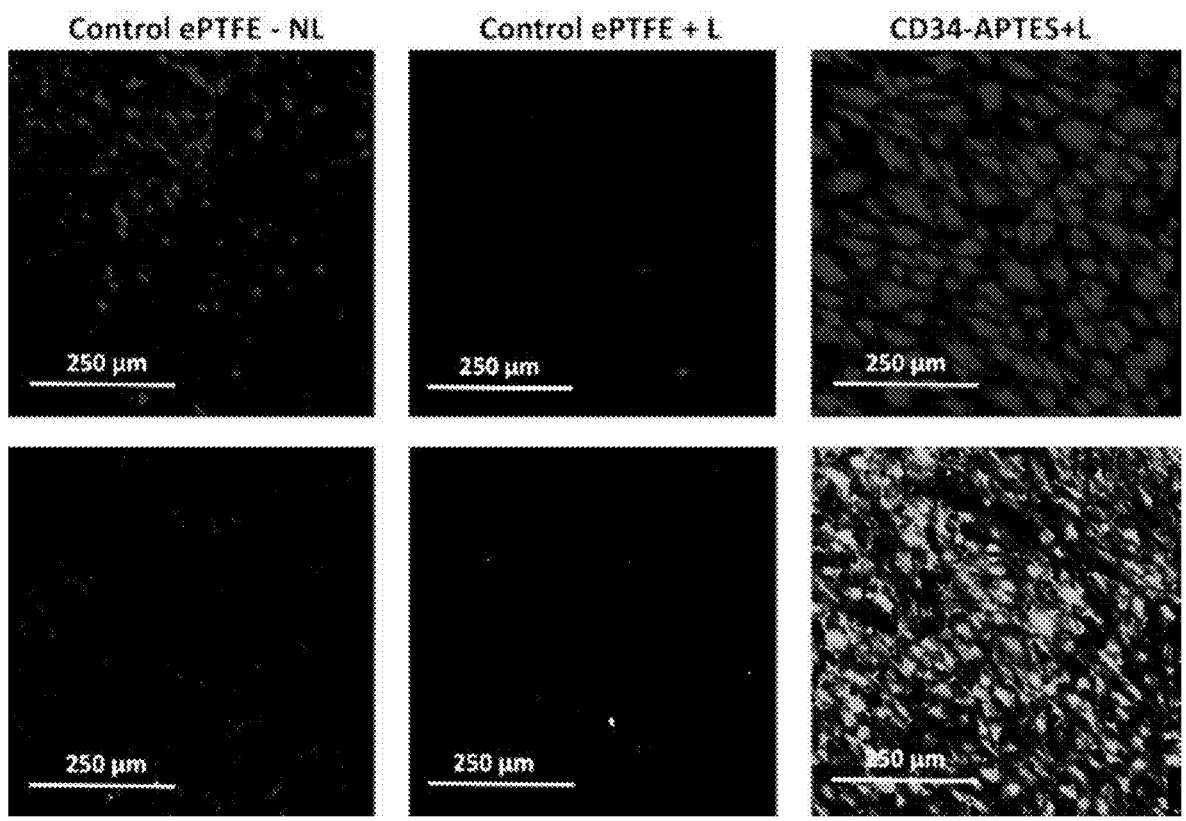

FIG. 15 shows long-term endothelial cell adhesion on control, exemplary lubricant-infused and optimized exemplary biofunctional lubricant-infused ePTFE surfaces.

Figure 16:
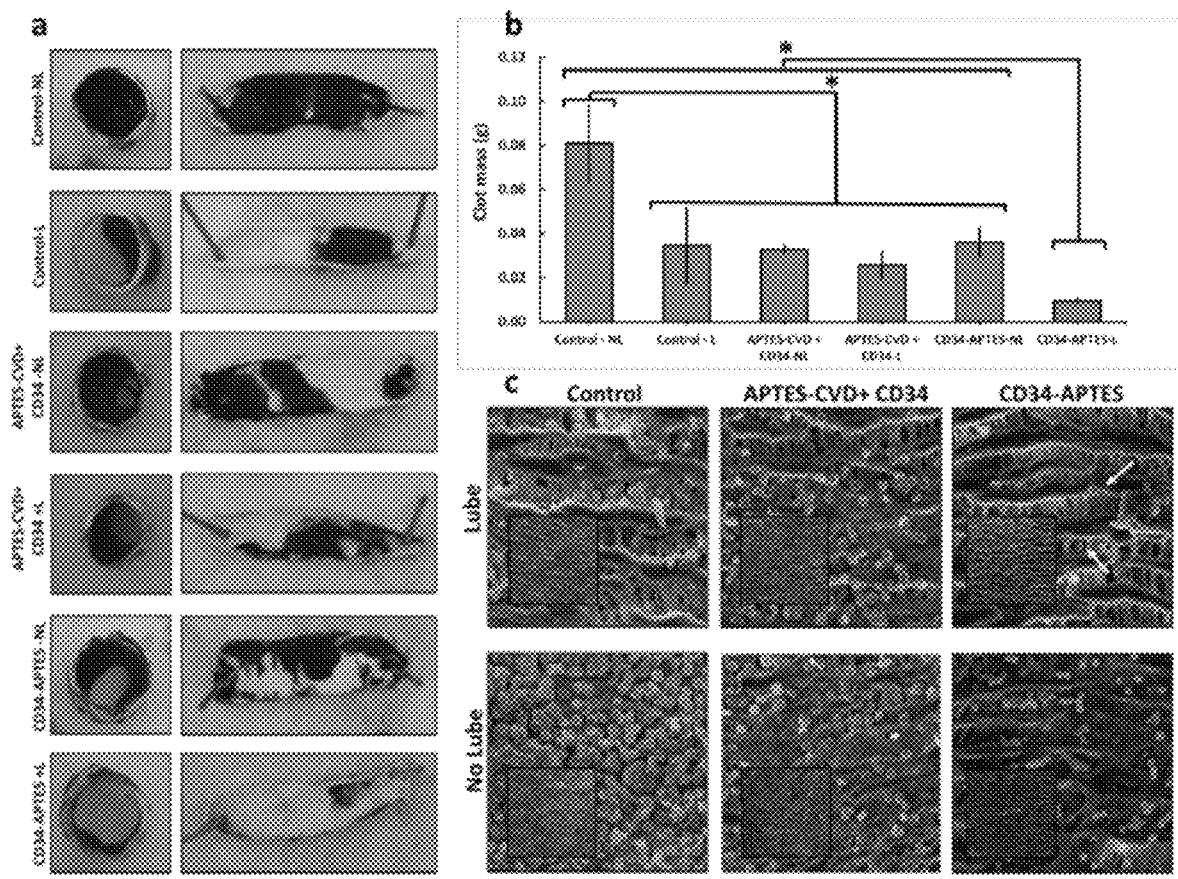

FIG. 16 shows blood clot and cell adhesion on exemplary modified and control ePTFE surfaces. a) Images of blood clot formation and adhesion on ePTFE vascular grafts incubated with whole human blood. b) Whole human blood clot mass attached to modified and control ePTFE grafts. c)

SEM images of ePTFE grafts, after the whole human blood clotting experiment. Bars show means±SD of at least three samples. *P<0.05.

Figure 17:
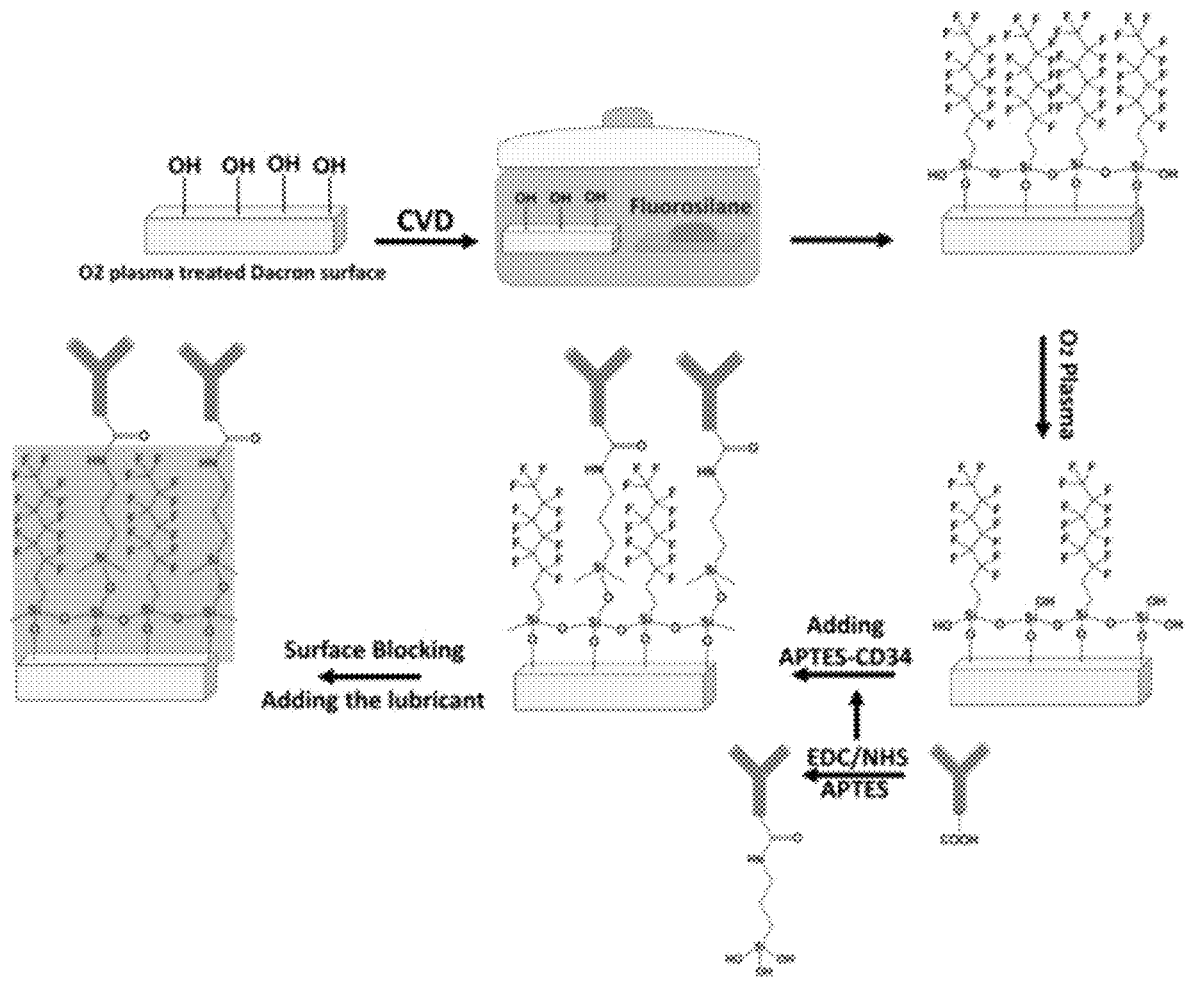

FIG. 17 shows a schematic representation of exemplary CD34-APTES treatment of the exemplary fluorosilanized PET surfaces as in Example 3. PET surfaces were initially oxygen plasma treated and further CVD treated using trichloro(1H,1H,2H,2H-perfluorooctyl) silane (TPFS). A secondary oxygen plasma treatment was applied on the TPFS treated surfaces in order to partially etch the TPFS layer and generate hydroxyl groups on the surface. Further, CD34-APTES functionalized antibodies were covalently attached to the hydroxyl functionalized TPFS treated surfaces using EDC/NHS chemistry. In the final step, biofunctionalized surfaces were blocked by adding perfluoroperhydrophenanthrene (PFPP) lubricant to the surfaces and biofunctionalized lubricant-infused PET surfaces were generated.

Figure 18:
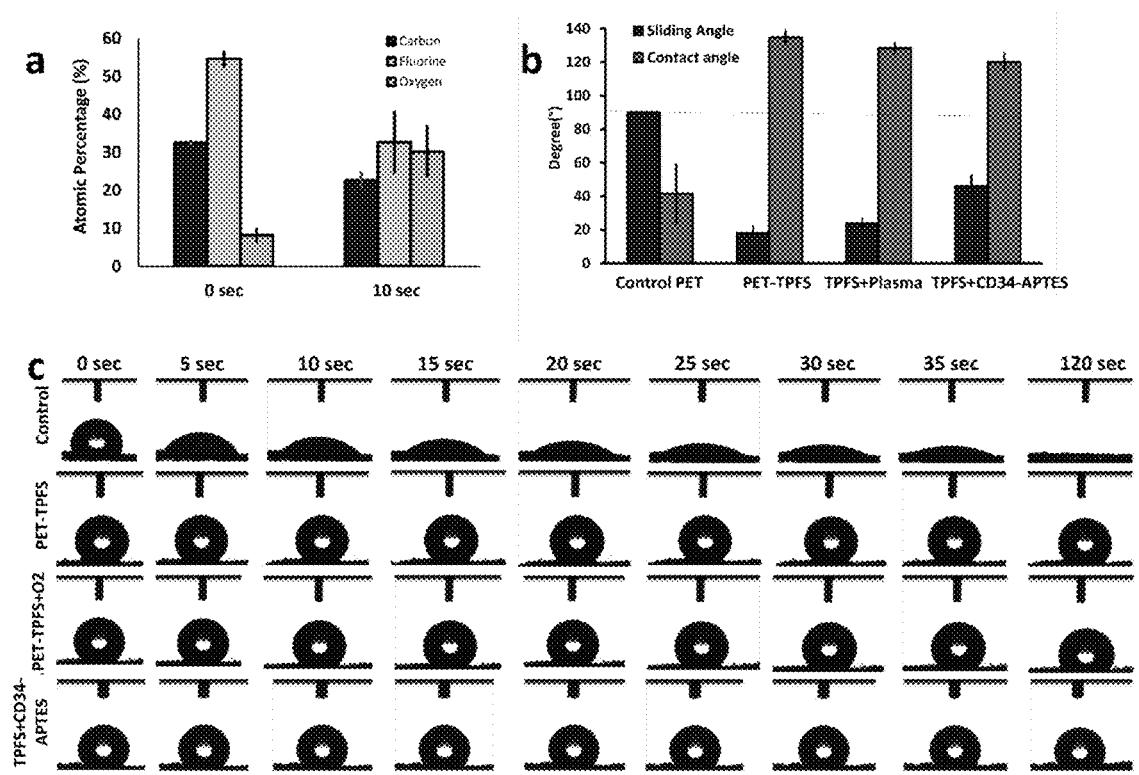

FIG. 18 shows the surface chemical composition and the contact and sliding angle measurements of control-PET, PET-TPFS, PET-TPFS+oxygen plasma and exemplary biofunctionalized lubricant infused (BLIS, TPFS+CD34-APTES) surfaces. a) The atom% of fluorine and oxygen was assessed using XPS. b) Sliding and contact angle measurements on control, lubricant infused and BLIS. c) The water-substrate interaction was investigated at different time points after adding a 5 µl droplet on the surfaces and the contact angle was measured.

Figure 19:
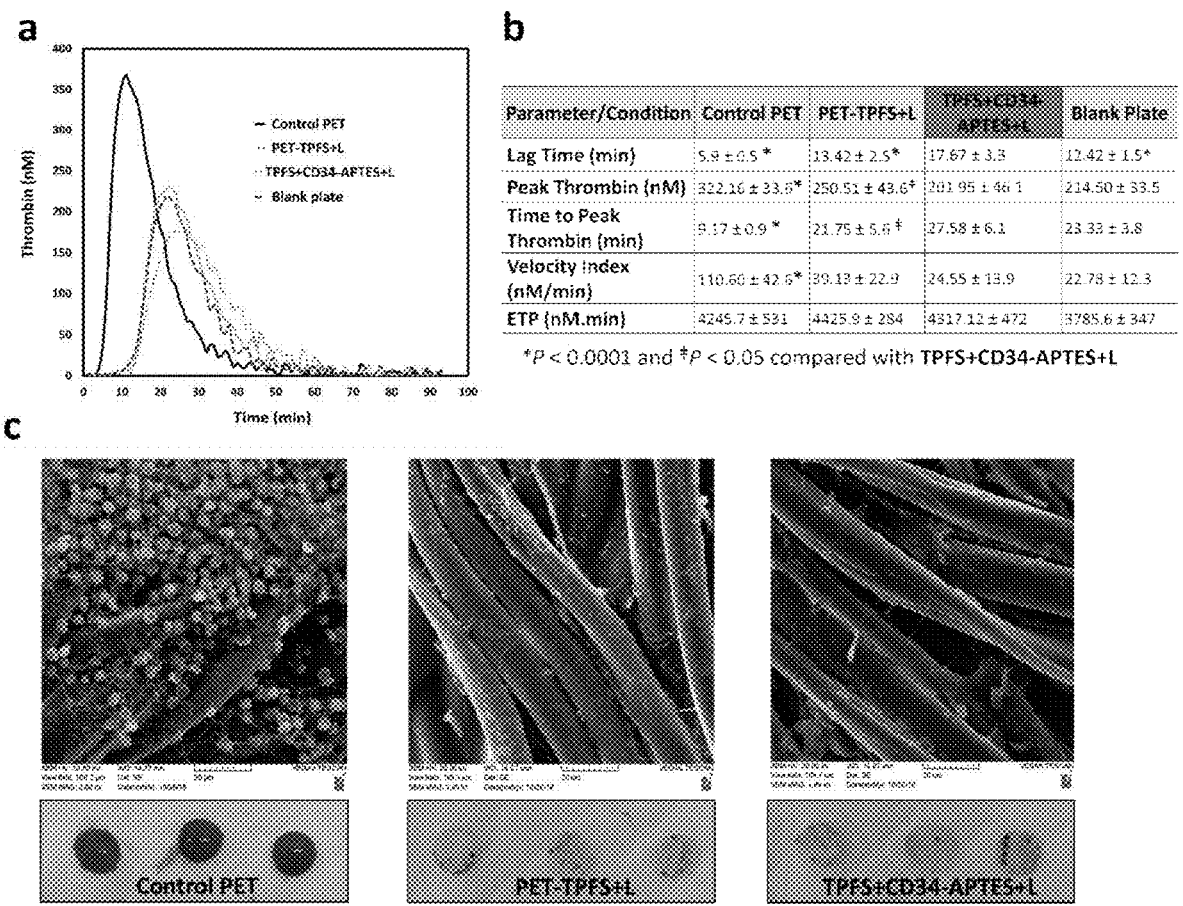

FIG. 19 shows results thrombin generation and clot formation on exemplary modified and control surfaces. a) A representative thrombin vs. time plot is shown. b) Thrombin generation parameters were determined in empty wells or wells containing control or modified PET surfaces. c) Whole human blood clot formation on control-PET, PET-TPFS+L and biofunctionalized lubricant-infused surfaces.

Figure 20:

FIG. 20 shows the bioactivity and targeting features of the exemplary biofunctionalized lubricant-infused PET surfaces. Modified and control PET surfaces were incubated with RFP-HUVECs in blood for 4 days and cell attachment was investigated.

DESCRIPTION OF VARIOUS EMBODIMENTS

I. DEFINITIONS

Unless otherwise indicated, the definitions and embodiments described in this and other sections are intended to be applicable to all embodiments and aspects of the present application herein described for which they are suitable as would be understood by a person skilled in the art.

The term "and/or" as used herein means that the listed items are present, or used, individually or in combination. In effect, this term means that "at least one of" or "one or more" of the listed items is used or present.

As used in the present application, the singular forms "a", "an" and "the" include plural references unless the content clearly dictates otherwise. For example, an embodiment including "a surface" should be understood to present certain aspects with one surface or two or more additional surfaces.

In embodiments comprising an "additional" or "second" component, such as an additional or second surface, the second component as used herein is different from the other components or first component. A "third" component is different from the other, first, and second components, and further enumerated or "additional" components are similarly different.

In understanding the scope of the present application, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives.

The term "consisting" and its derivatives, as used herein, are intended to be closed terms that specify the presence of the stated features, elements, components, groups, integers, and/or steps, but exclude the presence of other unstated features, elements, components, groups, integers and/or steps.

The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

The term "suitable" as used herein means that the selection of the particular compound or conditions would depend on the specific synthetic manipulation to be performed, and the identity of the molecule(s) to be transformed, but the selection would be well within the skill of a person trained in the art. All process/method steps described herein are to be conducted under conditions sufficient to provide the product shown. A person skilled in the art would understand that all reaction conditions, including, for example, reaction solvent, reaction time, reaction temperature, reaction pressure, reactant ratio and whether or not the reaction should be performed under an anhydrous or inert atmosphere, can be varied to optimize the yield of the desired product and it is within their skill to do so.

The expression "proceed to a sufficient extent" as used herein with reference to the reactions or process/method steps disclosed herein means that the reactions or process/method steps proceed to an extent that conversion of the starting material or substrate to product is optimized for a given set of conditions. Conversion may be optimized when greater than about 5, 10, 15, 20, 25, 30, 35, 40, 45, 50, 55, 60, 65, 70, 75, 80, 85, 90, 95 or 100% of the starting material or substrate is converted to product.

The terms "about", "substantially" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies or unless the context suggests otherwise to a person skilled in the art.

The present description refers to a number of chemical and biological terms and abbreviations used by those skilled in the art. Nevertheless, definitions of selected terms are provided for clarity and consistency.

The term "reactive functional group" as used herein refers to a group of atoms or a single atom that will react with another group of atoms or a single atom (so called "complementary functional group") to form a chemical bond between the two groups or atoms.

The term "reacts with" as used herein generally means that there is a flow of electrons or a transfer of electrostatic charge resulting in the formation of a chemical bond.

The term "perfluorocarbon oil" as used herein refers to a compound comprising carbon, fluorine and optionally one or more heteroatoms that is a liquid at ambient temperature (e.g. a temperature of about 4° C. to about 40° C. or about 25° C.).

The term "perfluorocarbon group" as used herein refers to a functional group comprising carbon, fluorine and optionally one or more heteroatoms.

The term "perfluoroalkane" as used herein means a straight or branched chain, saturated alkane, in which each hydrogen atom has been replaced with a fluorine atom. In some embodiments of the present application the number of carbon atoms that are possible in a referenced perfluoroalkane are indicated by the numerical prefix "$C_{n1-n2}$". For example, the term $C_{5-12}$perfluoroalkane means a perfluoroalkane having 5, 6, 7, 8, 9, 10, 11 or 12 carbon atoms.

The term "perfluoroalkyl group" as used herein, whether it is used alone or as part of another group, means a straight or branched chain, saturated alkyl group, in which each hydrogen atom has been replaced with a fluorine atom. In some embodiments of the present application the number of carbon atoms that are possible in a referenced perfluoroalkyl group are indicated by the numerical prefix "$C_{n1-n2}$". For example, the term $C_{3-12}$perfluoroalkyl means a perfluoroalkyl group having 3, 4, 5, 6, 7, 8, 9, 10, 11 or 12 carbon atoms.

The term "perfluoroalkylene group" as used herein, whether it is used alone or as part of another group, means a straight or branched chain, saturated alkylene group, in which each hydrogen atom has been replaced with a fluorine atom.

The term "perfluorohaloalkane" as used herein means a straight or branched chain, saturated haloalkane (i.e. an alkane that has been substituted with at least one halo substituent e.g. bromo, in which case the perfluorohaloalkane is referred to herein as a "perfluorobromoalkane"), in which each hydrogen atom has been replaced with a fluorine atom. In some embodiments of the present application the number of carbon atoms that are possible in a referenced perfluorohaloalkane e.g. a perfluorobromoalkane are indicated by the numerical prefix "$C_{n1-n2}$". For example, the term $C_{5-12}$perfluorobromoalkane means a perfluorobromoalkane having 5, 6, 7, 8, 9, 10, 11 or 12 carbon atoms.

The term "perfluorotrialkylamine" as used herein refers to a tertiary amine bearing three perfluoroalkyl groups that may be the same or different.

The term "perfluoroalkylether" as used herein refers to an ether bearing two perfluoroalkyl groups that may be the same or different.

The term "perfluoroalkylpolyether" as used herein refers to a polyether comprising perfluoroalkyl groups on each end with a repeat unit made up of alternating perfluoroalkylene groups and oxygen atoms.

The term "perfluorocycloalkane" as used herein means a mono- or bicyclic, saturated cycloalkane in which each hydrogen atom has been replaced with a fluorine atom. In some embodiments of the present application the number of carbon atoms that are possible in the referenced perfluorocycloalkane are indicated by the numerical prefix "$C_{n1-n2}$". For example, the term $C_{8-16}$perfluorocycloalkane means a perfluorocycloalkane having 8, 9, 10, 11, 12, 13, 14, 15 or 16 carbon atoms. In some embodiments, the perfluorocycloalkane group contains more than one cyclic structure or rings. When a perfluorocycloalkane group contains more than one cyclic structure or rings, the cyclic structures are fused, bridged, spiro connected or linked by a single bond. A first cyclic structure being "fused" with a second cyclic structure means the first cyclic structure and the second cyclic structure share at least two adjacent atoms therebetween. A first cyclic structure being "bridged" with a second cyclic structure means the first cyclic structure and the second cyclic structure share at least two non-adjacent atoms therebetween. A first cyclic structure being "spiro connected" with a second cyclic structure means the first cyclic structure and the second cyclic structure share one atom therebetween.

The term "alkyl" as used herein, whether it is used alone or as part of another group, means straight or branched chain, saturated alkyl group, that is a saturated carbon chain that contains substituents on one of its ends. The number of carbon atoms that are possible in the referenced alkyl group are indicated by the numerical prefix "$C_{n1-n2}$". For example, the term $C_{1-4}$alkyl means an alkyl group having 1, 2, 3 or 4 carbon atoms.

The term "alkane" as used herein means straight or branched chain, saturated alkane, that is a saturated carbon chain.

The term "alkylene" as used herein, whether it is used alone or as part of another group, means straight or branched chain, saturated alkylene group, that is a saturated carbon chain that contains substituents on two of its ends. The number of carbon atoms that are possible in the referenced alkylene group are indicated by the numerical prefix "$C_{n1-n2}$". For example, the term $C_{1-6}$alkylene means an alkylene group having 1, 2, 3, 4, 5 or 6 carbon atoms.

The term "halo" as used herein refers to a halogen atom and includes F, Cl, Br and I.

The term "amino" as used herein refers to the functional group $NH_2$ or $NHR^a$, wherein $R^a$ is $C_{1-6}$alkyl.

The term "hydroxyl" as used herein refers to the functional group OH.

The term "linker" as used herein refers to any molecular structure that joins two or more other molecular structures together.

The term "omniphobic" as used herein in respect to a surface refers to a surface with low wettability for both polar and nonpolar liquids.

The term "cell" as used herein refers to a single cell or a plurality of cells and includes a cell either in a cell culture or in a subject.

The term "atm" as used herein refers to atmosphere.

The term "MS" as used herein refers to mass spectrometry.

The term "aq." As used herein refers to aqueous.

DCM as used herein refers to dichloromethane.

DIPEA as used herein refers to N,N-diisopropyl ethylamine

DMF as used herein refers to dimethylformamide.

THF as used herein refers to tetrahydrofuran.

DMSO as used herein refers to dimethylsulfoxide.

EtOAc as used herein refers to ethyl acetate.

MeOH as used herein refers to methanol.

MeCN as used herein refers to acetonitrile.

HCl as used herein refers to hydrochloric acid.

TFA as used herein refers to trifluoroacetic acid.

CV as used herein refers to column volume.

Hex as used herein refers to hexanes.

PBS as used herein refers to phosphate-based buffer.

Epi as used herein refers to Eppendorf tubes.

MW as used herein refers to molecular weight.

HPLC as used herein refers to high performance liquid chromatography.

LCMS as used herein refers to liquid chromatography-mass spectrometry.

The term "antibody" as used herein refers to a full-length antibody molecule or an immunologically active portion of a full-length antibody molecule, i.e., a molecule that contains an antigen binding site that immunospecifically binds antigen of a target of interest or part thereof, such targets including but not limited to, cancer cells that produce specific identifiable antigens. The term "antibody" also refers to monoclonal antibodies, polyclonal antibodies, multispecific antibodies (e.g., bispecific antibodies), and antibody fragments. Antibodies may be murine, human humanized, chimeric, or derived from other species.

The term "self-assembled monolayers", "SAM", or the like as used herein refers molecular assemblies formed spontaneously on surfaces of substrates by adsorption and are organized into more or less large ordered domains. The SAMs of the present application are comprised of molecules possessing a silane-containing head group that has a strong affinity to the substrate and thereby anchors the molecule to the substrate.

The term "induce hydroxyl groups" or "form hydroxyl groups" as used herein means that the treatment of the substrate results in the presence of "OH" groups on its surface.

The term "biomolecules" as used herein refers to proteins, peptides, nucleic acids, lipids, enzymes and carbohydrates, and the like, and derivatives thereof.

The term "biospecies", "biospecies" and the likes as used herein refers to biomolecules, cells, viruses, bacteria, bacteriophage, and any other entity containing reactive functional groups that are complementary to reactive functional group on the silane-containing molecule and that one wishes to attach to a surface of a substate.

The term "biomarker" as used herein refers to any biospecies that is used to identify a specific target.

II. METHODS OF THE APPLICATION

Substrates, such as glass, polyethylene terephthalate (PET) and poly(methyl methacrylate (PMMA) are fluorosilanized using trichloro(1H,1H,2H,2H-perfluorooctyl)silane (TPFS) through either chemical vapor deposition (CVD) or liquid phase deposition (LPD) for creating self-assembled monolayers (SAMs) of TPFS onto the substrates. Prior to the silanization, the surfaces are activated via oxygen plasma treatment technique to induce hydroxyl groups onto the surface. Plasma treatment time and power are optimized for each substrate of interest. To perform CVD treatment, the plasma activated substrates are placed inside a vacuum desiccator (e.g. −0.8 MPa) with TPFS solution (e.g.200-500 uL) using a vacuum pump. The surfaces remain in the desiccator for about 1 to about 5 hours under the vacuum. Afterwards, they are cured in an oven or hotplate to further enhance the hydrolysis and condensation reactions and form the SAMs. The heat treatment can be done at, for example, about 100° C. for around, for example, 2 hours. It is possible to reduce the temperature to about 60° C. and keep the substrate for about 6 hours. Heat treatment parameters are modified according to the softening or melting point of the desired substrate. The CVD process can be automated using vacuum chambers with temperature and gas input controls for industrial applications.

Fluorosilanization of the substrate can also be performed by LPD method which is faster and more economical. In this method, TPFS solution is diluted in a solvent such as ethanol with the volume to volume percentage of about 2% to about 5%. Then, the plasma treated substrates are submerged inside the solution. The surfaces are maintained in the diluted TPFS bath for about 1 h. Afterwards, the surfaces are washed with water, ethanol, and 70% ethanol to remove the excess amount of the silane. The heat treatment process is done similar to the CVD method. Overall CVD has been shown to provide more homogeneous SAMs compared to LPD.

Therefore in one aspect, the present application relates to a method for producing biofunctional fluorosilinated substrates comprising a. coating a surface of a substrate with a fluorosilane to create at least one fluorosilane monolayer on the surface to provide a fluorinate surface on the substrate wherein the substrate comprises surface hydroxyl groups or has been treated to form surface hydroxyl groups;

b. etching the fluorosilinated surface on the substrate to provide reactive functional groups on at least a portion of the fluorosilinated surface of the substrate; and c. attaching biospecies to the reactive functional groups to obtain the biofunctional fluorosilinated substrates.

In some embodiments, the fluorosilane is a compound of the Formula I:

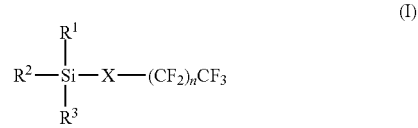

wherein
X is a single bond or is $C_{1-6}$alkylene,
n is an integer of from 0 to 12; and
$R^1$, $R^2$ and $R^3$ are each independently a hydrolysable group.

The hydrolysable group is any suitable hydrolysable group, the selection of which can be made by a person skilled in the art. In some embodiments, $R^1$, $R^2$ and $R^3$ are independently halo or —O—$C_{1-4}$alkyl. In some embodiments, $R^1$, $R^2$ and $R^3$ are all independently halo. In some embodiments, $R^1$, $R^2$ and $R^3$ are all independently —O—$C_{1-4}$alkyl. In some embodiments, $R^1$, $R^2$ and $R^3$ are all OEt. In some embodiments, $R^1$, $R^2$ and $R^3$ are all Cl.

In some embodiments, X is $C_{1-6}$alkylene. In some embodiments, X is $C_{1-4}$alkylene. In some embodiments, X is —$CH_2CH_2$—.

In some embodiments, n is an integer of from 3 to 12. In some embodiments, n is an integer of from 3 to 8. In some embodiments, n is an integer of from 4 to 6. In some embodiments, n is 5.

In some embodiments, $R^1$, $R^2$ and $R^3$ are all Cl, X is —$CH_2CH_2$— and n is 5. In some embodiments, $R^1$, $R^2$ and $R^3$ are all OEt, X is —$CH_2CH_2$— and n is 5. In some embodiments of the present application, the deposition comprises chemical vapor deposition followed by curing at elevated temperature under air.

In some embodiments, the fluorosilane is selected from any fluorocarbon-containing silanes such as, but not limited to, trichloro (1H,1H,2H,2H-perfluorooctyl)silane (TPFS), 1H,1H,2H,2H-perfluorooctyltriethoxysilane, 1H,1H,2H,2H-perfluorodecyltriethoxysilane, 1H,1H,2H,2H-Perfluorodecyltrichlorosilane, 1H,1H,2H,2H-perfluorodecyltrimethoxysilane, trimethoxy(3,3,3-trifluoropropyl)silane, (pentafluorophenyl)triethoxysilane and heptadecafluoro-1,1,2,2-tetra-hydrodecyl trichlorosilane. In some embodiments, the fluorosilane is selected from trichloro(1H,1H,2H,2H-perfluorooctyl)silane (TPFS) and 1H,1H,2H,2H-perfluorooctyltriethoxysilane (POTS).

In some embodiments the substrate that is treated to form surface hydroxyl groups is any substrate material that one wishes to functionalize using the methods of the application. In some embodiments, the substrate material is selected from a cement, polymer (e.g. polyvinyl chloride (PVC), polycarbonate (PC), polytetrafluoroethylene (PTFE), poly (methyl methacrylate) (PMMA), polystyrene, polyethylene terephthalate (PET) or a silicone elastomer such as a silicone elastomer comprising a polydimethylsiloxane (PDMS)), plastic, ceramic, metal (e.g. gold, aluminum, copper, stainless steel, titanium, zinc, copper, aluminium, magnesium, lead, pewter or tin-based alloys) or glass. In some embodiments, the substrate that comprises surface hydroxyl groups is glass.

In some embodiments the substrate is treated to form hydroxyl groups on a surface of the substrate using oxygen plasma. In some embodiments, the treatment comprises applying oxygen plasma for a time for the activation of the surface to proceed to a sufficient extent (e.g. a time of about 30 seconds to about 10 minutes or about 3 minutes).

In some embodiments the substrate is treated to form hydroxyl groups on a surface of the substrate using a chemical treatment with, for example, hydrogen peroxide, corona treatment, hydroxide containing solution, piranha solutions and/or oxygen plasma treatment.

The coating of the surface of the substrate with a fluorosilane to create at least one fluorosilane monolayer on the surface to provide a fluorosilinated surface on the substrate comprises any suitable process, the selection of which can be made by a person skilled in the art. For example, the skilled person would readily understand that the deposition comprises conditions which would hydrolyse the hydrolysable group to form a siloxane network. In an embodiment, the deposition comprises chemical vapor deposition followed by curing at a temperature and for a time for the hydrolysis of the hydrolysable group to form the siloxane network to proceed to a sufficient extent. In an embodiment, the curing comprises curing at elevated temperature (e.g. a temperature of from about 40° C. to about 80° C. or about 60° C.) under air for a time of about 4 hours to about 24 hours or about 16 hours. In another embodiment, the chemical vapor deposition comprises incubating the mold with the compound for a time of at least about 1 hour (e.g. a time of from about 1 hour to about 4 hours or about 1 hour to about 2 hours) under suitable vacuum pressure (e.g. a vacuum pressure of from about −0.06 MPa to about −0.09 MPa or about −0.08 MPa).

In some embodiments, the etching of the fluorosilinated surface on the substrate to provide reactive functional groups on at least a portion of the fluorosilinated surface of the substrate is plasma etching. In some embodiments, the plasma etching is performed by oxygen, air, carbon dioxide, argon or nitrogen plasma. In some embodiments, the plasma etching is performed by carbon dioxide plasma which forms both carboxyl ($CO_2H$) and hydroxyl (OH) groups on the substrate surface. In some embodiments, biospecies can be covalently attached to free carboxyl groups on the fluorosilinated surface via amine-carboxyl reactions. In some embodiments, the plasma etching is performed by oxygen plasma etching. In some embodiments, the oxygen plasma etching is performed for about 10 seconds to about 10 minutes, or about 20 seconds to about 7 minutes, about 30 seconds to about 5 minutes, or about 30 seconds to about 1 minute.

In some embodiments, the biospecies are selected from biomolecules, viruses, cells (bacteria, mammalian cells etc.), and combinations thereof. In some embodiments, the bio-molecules are selected from proteins, peptides, oligonucleotides, enzymes, and combinations thereof. In some embodiments, the viruses are bacteriophages.

In some embodiments, the biospecies are attached to the reactive functional groups using coupling agents. In some embodiments, the coupling agents are selected from one or more silanes comprising different reactive functionalities. In some embodiments, the silanes comprising different reactive functionalities are selected from, but are not limited to aminosilanes, glycidoxysilanes, alkanesilanes, epoxy silanes and the like. In some embodiments, the silane coupling agent is a compound of the Formula II:

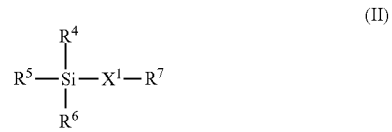

(II)

wherein
one or more of $R^4$, $R^5$ and $R^6$ is OH or a group that is converted by hydrolysis to OH, and the remaining of $R^4$, $R^5$ and $R^6$ is selected from $C_{1-6}$alkyl,,
$X^1$ is linker; and
$R^7$ is a reactive functional group that reacts with a complementary functional group on a biospecies to form a covalent bond.

The group that is converted by hydrolysis to OH is any suitable hydrolysable group, the selection of which can be made by a person skilled in the art. In some embodiments, the hydrolysable group is halo or $-O-C_{1-4}$-etalkyl.

In some embodiments, $X^1$ is $C_1-C_{20}$alkylene, $C_2-C_{20}$alkenylene or $C_2-C_{20}$alkynylene, each of which is optionally interrupted by O or C(O). In some embodiments, $X^1$ is $C_{1-20}$alkylene. In some embodiments, X is $C_{1-10}$alkylene.

In some embodiments $R^7$ is an amino group, an epoxide, a glycidoxy group

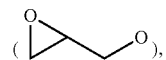

a carboxylic acid ($CO_2H$), an aldehyde (COH), an ester ($CO_2R^b$, wherein $R^b$ is $C_{1-6}$alkyl, benzyl, etc.), a tosyl group, halo, isocyanato (NCO), and the like. In some embodiments, $R^7$ is $NH_2$, $CO_2H$ or glycidoxy.

In some embodiments, the silane coupling agent is selected from 3-(trimethoxysilyl) propyl aldehyde, 3-(triethoxysilyl) propyl isocyanate, 3-glycidoxypropyltrimethoxysilane, (3-glycidyloxypropyl)trimethoxysilane and aminopropyltrimethoxy silane (APTES).

In some embodiments, when a coupling agent is used to attach the biospecies to the reactive functional groups, the reactive functional groups on at least a portion of the fluorosilinated surface of the substrate are first reacted with a first end of the coupling agent followed by reaction of the biospecies to a second end of the coupling agent to obtain the biofunctional fluorosilinated substrates.

In some embodiments, the biospecies is functionalized to allow them to covalently attach directly to the reactive functional groups on the substrate surface. In some embodiments, prior to attaching the biospecies to the substrate's surface, carboxyl groups (COOH) present on the biospecies are modified with an amino-based coupling agent such as APTES in solution. The modified biospecies may then be immobilized on hydroxyl (OH) terminated surfaces on the substrate using, for example, $O_2$ plasma treatment. After functionalization of the biospecies with the coupling agent, they are purified and filtered by performing different purification steps on the modified biospecies solution such as dialyzing the biospecies solution and, optionally, lyophilizing. This ensures that all of the unreacted silane coupling agents and other impurities generated during the reaction are removed from the functionalized biospecies so that it can be stored for long periods of time.

In some embodiments, to silanize proteins or antibodies of interest with APTES, for instance, EDC-NHS chemical reactions are employed using MES buffer. The proper ratio of silane to protein or antibody will be calculated based on the available groups on the antibody or protein of choice (e.g. anti IL6). It should be mentioned that the concentration of the amino-based silane coupling agent plays a role in the protein/antibody functionalization. In some embodiments, the concentration of the functionalized antibodies or proteins will be controlled by adjusting the concentration of the silane coupling agent. Epoxy-based silane coupling agents such as (3-glycidyloxypropyl)trimethoxysilane are an alternative reagent that can be used to prepare functionalized biospecies. Here, the epoxide at a first end of the couple agent can directly react with a primary amine or a secondary amine of the biospecies, such as a protein to produce a secondary amine plus hydroxyl or a tertiary amine plus hydroxyl, respectively. The benefit of this silane coupling agent is that there is no need for using carbodiimide chemistry to pre-active any functional group.

By functionalizing the biospecies to allow them to covalently attach directly to the reactive functional groups on the substrate surface, it is an embodiment that such materials are called "biofunctional inks" or "bioinks". In some embodiments, antibody biofunctional inks are attached to substrates prepared using secondary plasma treatment techniques, followed by lubricant treatment, which provides biofunctional lubricant-infused surfaces possessing hydroxylate groups. In some embodiments, the biospecies ink or solution is patterned on the substrates using both non-contact printing and contact printing. In some embodiments, the biospecies are attached to the plasma-treated fluorosilinated surfaces using conventional liquid phase deposition, droplet-dispensing non-contact printing, microcontact printing, contact printing or any other immobilization methods.

The biospecies (e.g. antibody) biofunctional inks can be frozen after the functionalization. Thus, they can be stored for a long time and used once needed.

In some embodiments, the method for preparing biofunctional fluorosilinated surfaces further comprises coating the biofunctional fluorosilinated surface with a fluorinated lubricant following attachment of the biomolecule. In some embodiments, the lubricant is a perfluorocarbon oil. In another embodiment, the perfluorocarbon oil is a perfluorotrialkylamine (e.g. a $C_{3-7}$perfluorotrialkylamine such as perfluorotripentylamine), a perfluoroalkylether or perfluoroalkylpolyether (e.g. a polymer of polyhexafluoropropylene oxide of the formula F—$(CF(CF_3)$—$CF_2$—$O)_m$—$CF_2CF_3$, wherein m is an integer of from 10 to 60), a perfluoroalkane (e.g. a $C_{5-12}$perfluoroalkane such as perfluorohexane or perfluorooctane), a perfluorocycloalkane (e.g. perfluorodecalin or perfluororperhydrophenanthrene) or a perfluorohaloalkane, wherein halo is other than fluoro (e.g. a $C_{5-12}$perfluorobromoalkane such as bromoperfluorooctane). In some embodiments, the lubricant is a perfluorocycloalkane. In some embodiments, the lubricant is a $C_{8-16}$perfluorocycloalkane. In some embodiments, the lubricant is perfluorodecalin or perfluoroperhydrophenanthrene.

In some embodiments, the present application also includes a method of producing a purified silanized biospecies comprising:
a. reacting a biospecies with a silane-containing molecule, wherein the silane containing molecule comprises a functional group that reacts with a complementary functional group on the biospecies and a silane functional group of the formula —$SiR^8R^9R^{10}$,
wherein one or more of $R^8$, $R^9$ and $R^{10}$ is OH or a group that is converted by hydrolysis to OH, and the remaining of $R^8$, $R^9$ and $R^{10}$ is selected from $C_{1-6}$alkyl,
and the biospecies and the silane-containing molecule are reacted under conditions to produce the silanized biospecies;
b. purifying the silanized biospecies under conditions to remove excess of the silane-containing molecule; and
c. optionally producing a storage solution or powder of the purified silanized biospecies.

In some embodiments, the biospecies are selected from proteins, peptides, antibodies, oligonucleotides, enzymes, viruses, cells, and any other species with one or more functional groups selected from amine and carboxyl groups.

In some embodiments, the functional group that reacts with a complementary functional group on the biospecies is amino group, an epoxide, a glycidoxy group

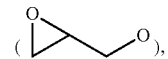

a carboxylic acid ($CO_2H$), an aldehyde (COH), an ester ($CO2R^b$, wherein $R^b$ is $C_{1-6}$alkyl, benzyl, etc.), a tosyl group, halo, isocyanato (NCO), and the like. In some embodiments, the functional group that reacts with a complementary functional group on the biospecies is an amino, epoxide, glycidoxy or carboxylic acid group. In some embodiments, the silane functional group of the formula is triethoxysilane or trimethoxysilane. In some embodiments, the silane-containing molecule is APTES or 3-glycidyloxypropyl)trimethoxysilane, or the like, In some embodiments, to silanize proteins or antibodies of interest with APTES, for instance, EDC-NHS chemical reactions are employed using MES buffer. The proper ratio of silane to protein or antibody will be calculated based on the available functional groups on the biospecies, such as an antibody or protein of choice (e.g. anti IL6). Epoxy-based silane coupling agents such as (3-glycidyloxypropyl)trimethoxysilane are an alternative reagent that can be used to prepare functionalized biospecies. Here, the epoxide at a first end of the couple agent can directly react with a primary amine or a secondary amine of the biospecies, such as a protein to produce a secondary amine plus hydroxyl or a tertiary amine plus hydroxyl, respectively. The benefit of this silane coupling agent is that there is no need for using carbodiimide chemistry to pre-active any functional group.

Conditions to silanize other biospecies using other silane-containing molecules can be determined using methods known in the art.

In some embodiments, the biospecies is reacted with a silane-containing molecule in a buffer solution. In some embodiments, the buffer solution has a pH of about 4-7 or about 5-6.

In some embodiments, the removing of the excess silane-containing molecule is by dialyzing the silanized biospecies in solution. In some embodiments, the dialysis is done for a minimum of 4, 6 or 8 cycles. In some embodiments, the dialysis is performed in a dialysis membrane having a molecular weight cut off appropriate for the biospecies, for example, about 3 kDa to about 6 kDa, or about 3.5 kDa to about 5 kDa.

In some embodiments, a powder of the dialysized silanized biospecies is made by lyophilization.

In some embodiments, the biospecies used in the methods for preparing biofunctional fluorosilinated surfaces are the purified silanized biospecies prepared this method of the present application, and they are covalently attached to the fluorosilinated surface via the Si—OH moieties and are stable under extensive washing and flow.

In some embodiments, the pure silanized biospecies are useful for antibody, biomolecule and cell detection and separation.

In some embodiments, the biospecies are viruses. In some embodiments, the pure silanized biospecies are silanized viruses. In some embodiments, the viruses are bacteriophages. In some embodiments, the silanized viruses are covalently attached onto devices for drug delivery, gene delivery or to express certain desired moieties or sequences. In some embodiments, the silanized viruses are covalently attached to interfaces for antibacterial or biosensing applications.

In some embodiments, the biospecies are cells which are covalently attached onto devices for applications in tissue engineering, synthetic biology, single cell study, drug screening, drug delivery, gene delivery, and/or robotics.

III. EXAMPLES

The following non-limiting examples are illustrative of the present application:

Example 1

Preparation of Fluorosilanized Surfaces

Glass microscope slides were used as initial substrates in the experiments. Glass microscope slides were cut in to smaller pieces and oxygen plasma treated for 2 minutes in order to activate their surfaces for attaching the fluorosilane molecule. After plasma treating the substrates, they were placed in a desiccator containing 200 µL of trichloro (1H, 1H,2H,2H-perfluorooctyl) silane. Further, the vacuum was turned on and the CVD reaction was initiated. After 2 hours of CVD treatment, samples were removed from the desiccator and cured at 60° C. for 12 hours.

Example 2

Post Plasma Treating the Fluorosilanized Surfaces

In order to further enhance the number of hydroxyl groups on the surface after the fluorosilanization and baking, a secondary short plasma treatment with oxygen gas was performed on the substrate. Inducing more hydroxyl groups on the surface can promote the biofunctionality of the surface for the biomolecule immobilization. The secondary plasma treatment can also deteriorate the fluorine groups on the surface to some extent, thereby reducing the hydrophobicity of the surface and capability to lock the lubricant. Thus, the time of plasma treatment was optimized to ensure that the acceptable amount of fluorine groups remains on the surface after the secondary plasma activation. Secondary plasma treatment is also useful when contact printing is used to print the biomolecules onto the surface After removing the glass samples from the oven and after completing the fluorosilanization step, glass substrates were exposed to different oxygen plasma treatment times in order to create hydroxyl functional groups on the silanized surfaces. Glass samples were placed in a plasma machine, operated with oxygen and treated for 10, 60 and 300 seconds.

Figure 1:
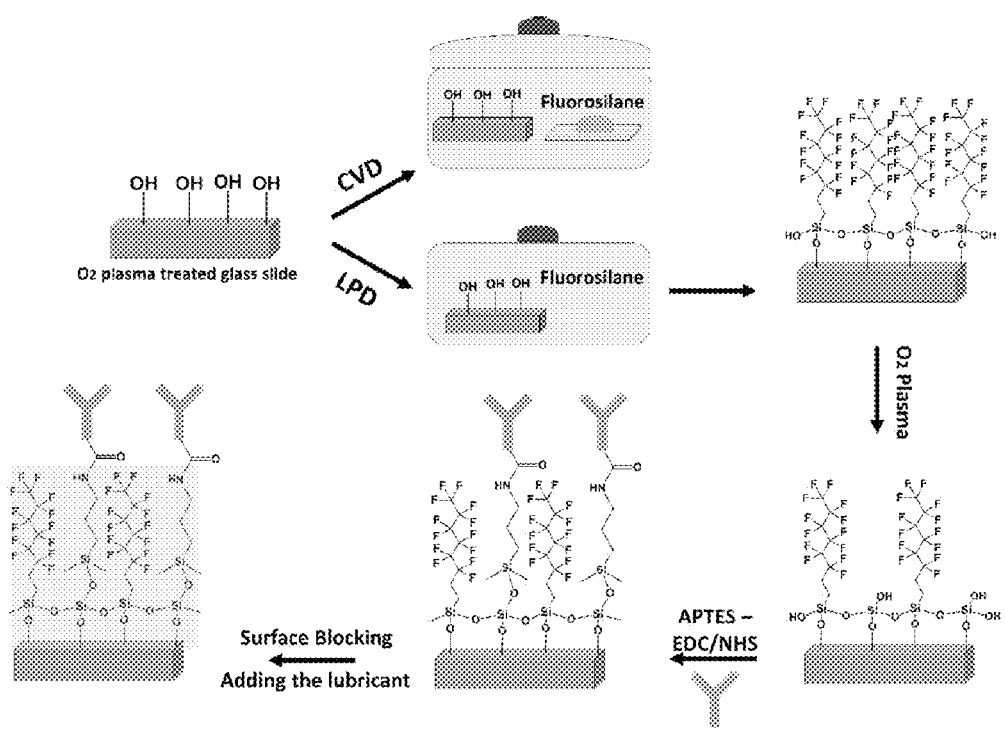
Figure 2:
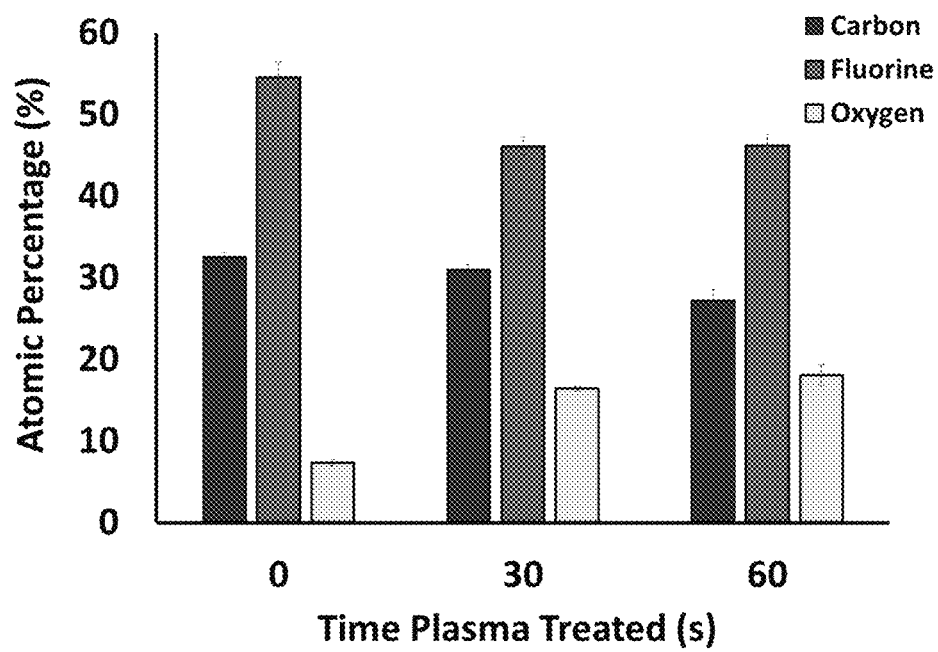
FIG. 2 shows the X-ray photoelectron spectroscopy (XPS) results obtained after different oxygen plasma treatment times of exemplary fluorosilanized substrates.

Surfaces were subject to different oxygen plasma exposure times and the atom % of fluorine, oxygen and carbon were calculated using XPS. As seen in the FIG. 2, by increasing the oxygen plasma time, the atom % of oxygen increases while the atom % of fluorine decreases, confirming the etching of the fluorine molecules and the generation of hydroxyl functional groups on the surface. The results also indicate that the amount of functional groups generated on the surface can be tuned by changing the plasma treatment time.

Example 3

Sliding and Contact Angle Measurements

Sliding and contact angle measurements were performed on post-plasma treated fluorosilanized surfaces in order to investigate their blocking properties. After plasma treating surfaces for different exposure times, a fluorinated lubricant was added to the surfaces in order to create the repellent lubricant infused surface. Sliding angles were measured by placing a 5 µL droplet on the lubricated surfaces and gently tilting the surface until the droplet started to slide. The minimum angle required for the droplet to move on the surface was recorded as the sliding angle. Water sessile drop contact angle measurements were performed at room temperature after modifying the glass slides with fluorosilane molecules and after oxygen plasma treating them using a Future Digital Scientific OCA20 goniometer.

Figure 3:
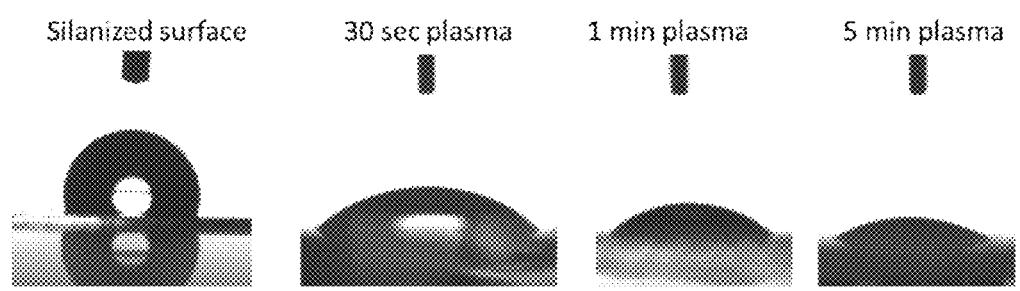
FIG. 3 shows pictures of exemplary fluorosilanated substrates after various plasma oxygen treatment times.

As shown in Table 1 and FIG. 3, after plasma treating the fluorosilanated substrate, the surfaces become more hydrophilic in some areas, which indicates the creation of hydrophilic hydroxyl domains after the plasma treatment.

TABLE 1

| FS-CVD | <5 | 103 |
| 30 sec plasma | <15 | 44.34 |
| 1 min plasma | <15 | 28.29 |
| 5 min plasma | <15 | 22.34 |

Example 4

Preparing Antibody Functionalized Surfaces

The post $O_2$ plasma treated fluorosilanized surfaces were functionalized with APTES and antiCD34 antibodies in order to investigate their ability for capturing biomolecules on them. Surfaces treated with different plasma times were modified with APTES as a coupling agent and later on the APTES molecules were functionalized with anti-CD34 antibody by incubating the APTES-modified surfaces with the antiCD34 antibody solution for 12 hours at 37° C. The antibody solution was removed from the substrates and surfaces were washed with DI water and PBS in order to remove the non-covalent attached antibodies. The results are shown in FIGS. 4a and 4b.

Example 5

Post Functionalization of Treated Surfaces

After adding the primary antibody to the post plasma treated fluorosilanized substrates, the substrates were blocked by adding a lubricant layer onto their surfaces. In order to investigate the biofunctionality and blocking properties of the modified surfaces and to confirm the functionalization of the attached anti-CD34 antibodies on the surface, the secondary antibody (Goat anti-Mouse IgG Secondary Antibody, Alexa Fluor 594) was added to the substrates. Surfaces coated with the primary antibody and lubricated with perfluorodecalin were incubated with 100 uL of goat anti-mouse IgG antibody for 2 hours. Subsequently, the samples were removed from the solution, washed with DI water and PBS. The degree on the attachment of the secondary antibody to the surface was investigated by fluorescence microscopy. The results are shown in FIGS. 4a and 4b.

Example 5

Preparation of Silanized Biospecies

Proteins and antibodies (e.g. anti-CD34 antibody, BSA, Avidin) were silanized with aminopropyltriethoxysilane (APTES) as a model coupling agent using the EDC/NHS chemistry. The chemical reaction was carried out in MES buffer (pH 5.5) for 2 hr. Initially, protein was added to the MES buffer (obtaining the desired concentration) and then 0.2 M EDC and 0.7 M NHS were added to the solution. In a subsequent step APTES was added to the mixture and the solution was left stirring at room temperature for 2 h. The solution mixture was transformed to dialysis membranes (molecular weight cut off 3.5-5 kDa) and dialyzed for four to six cycles in order to purify the protein mixture from non-reacted APTES molecules. Further, the protein solution was lyophilized to complete the purification step. The protein powder was kept at 4° C. prior to any further surface modification steps. This reaction sequence is shown schematically in FIG. 5.

As seen in FIG. 6, after modifying the BSA with the APTES coupling agent, an increase in the protein molecular weight was observed which indicates the successful covalent attachment of the APTES molecules to the protein.

Example 6

Functionalizing Surfaces with Silanized Proteins

Glass substrates were washed and sonicated with ethanol and dried with nitrogen gas. Prior to adding the obtained protein solution (from Example 5) to the glass surfaces, the surfaces of the glass substrates were activated using an $O_2$ plasma machine in order to obtain a high concentration of OH groups on the surface. Once the glass substrates were plasma treated, 200 μL of the protein solution was added to each glass substrate and the surfaces were incubated with the protein solution at 37° C. for 5 hours. The protein solution was then removed from the glass substrates and samples were washed with MES and DI water (three times) in order to insure the removal of non-covalent attached proteins. The surfaces were then imaged using a fluorescence microscope to confirm the presence of the immobilized biomolecules.

As shown in FIG. 7, the Si—O—Si stretch seen in the spectrum, confirms the covalent attachment of the BSA-APTES molecule to the surface.

Example 7

Stability Test

After modifying the substrates with the APTES-protein (Example 6), the stability of the coating was investigated using multi-step washing tests. After coating the surfaces, samples were initially washed with PBS and fluorescence images were taken and the fluorescence intensity was measured using ImageJ. Samples were incubated for 24 h, 48 h and 2 weeks in the TBST buffer and images were taken after each step. As seen in FIG. 8, the coating remained stable when compared to physically adsorbed surfaces and no significant difference was seen when comparing the results with the conventional coating system.

Surfaces were modified with fluorescently labeled anti-CD34 antibody, washed and incubated with Tris buffered saline with Tween-20 (TBST) for over 2 weeks and the fluorescent intensity of the modified surfaces was measured and compared to control samples. Surfaces functionalized using the conventional technique (chemical vapor deposition of APTES and then functionalization with anti-CD34 antibody) and physical adsorption of anti-CD34 antibody were used as control samples and the results were compared to surfaces modified with our proposed technique. Samples modified with our proposed technique remained highly stable even after 2 weeks of being in solution. Results are shown in FIGS. 8(a) and 8(b).

Example 8

Bio-Functionality of the Coating

The post functionality of the coated APTES-anti-CD34 antibodies was measured by investigating the ability of the antibodies to bind to a secondary antibody. Mouse anti-human CD34 antibody (conjugated with Alexa Fluor 488) was used as the primary antibody and modified with APTES and goat anti-mouse IgG antibody (conjugated with Alexa Fluor 594) was used as the secondary antibody to investigate the functionality of the anti-CD34 antibody after the chemical modification step. As seen in FIG. 9, both in solution and after micro-contact printing, the modified primary antibody stays highly functional and successfully binds to the secondary antibody.

Example 9

Thrombin Generation Assay

Surfaces that are bio-functional in order to capture cells and specific biomolecules are highly investigated in biomedical applications. These surfaces have to be biocompatible and blood repellent. In order to investigate the ability of the present APTES-anti-CD34 antibody coated surfaces in attenuating clot formation, a thrombin generation assay was performed as previously described [33]. Briefly, samples were placed in a 96 well polytetrafluoroethylene (PTFE) plate and incubated with citrated plasma at 37° C. for 5 mins. The thrombin generation reactions were initiated by adding FluCa, a mixture of $CaCl_2$ and fluorescent substrate (Thrombinoscope). Measurements were taken using a Labsystems Fluoroskan Ascent FL plate reader (MTX Lab Systems, Inc, Vienna, Va., USA) plate reader for 2 h and 30 min hours at 1 min intervals. As seen in FIG. 10, samples modified with the molecules of the present application acted better than both the control substrates and surfaces modified with the conventional modification technique. The modified surfaces significantly reduced the amount of thrombin generated, time to peak thrombin and the lag time.

Example 10

Lubricant Infused ePTFE Grafts Biofunctionalized Using Silanized Anti-CD34 Antibodies Prevent Thrombin Generation and Promote Endothelialization Materials Perfluoroperhydrophenanthrene (PFPP), 3-aminopropyl-triethoxy-silane (APTES), N-(3-Dimethylaminopropyl)-N'-ethylcarbodiimide (EDC), N-Hydroxysuccinimide (NHS), 2-(N-Morpholino) ethanesulfonic acid (MES), spectra-por float-a-lyzer G2 dialysis tubes were purchased from Sigma-Aldrich (Oakville, Canada). Alexa Fluor 488 conjugated mouse anti-human CD34 antibody and trypsin-EDTA (0.25%) were purchased from ThermoFisher Scientific (Massachusetts, United States). Red Fluorescent Protein Expressing Human Umbilical Vein Endothelial Cells (RFP-HUVEC) were generously donated by Dr. P. Ravi Selvaganapathy's lab at McMaster University. Cell media kit (EGM-2 BelletKit) and trypsin neutralizing agent where purchased from Cedarlane (Burlington, Canada). The thrombin-directed fluorescent substrate, Z-Gly-Gly-Arg-AMC, was purchased from Bachem (Bubendorf, Switzerland). Teflon (ePTFE) vascular grafts were kindly provided by Hamilton Health Sciences (Hamilton, ON). Whole human blood and pooled citrated plasma was generated from blood samples collected from healthy donors as previously described [34]. A signed written consent was collected from donors and all procedures were approved by the McMaster University Research Ethics Board.

MethodsS (a) Preparing APTES Functionalized Anti-CD34 Antibody (CD34-APTES)

Anti-CD34 antibody was silanized with APTES using the EDC/NHS carbodiimide crosslinker chemistry. Anti-CD34 antibody solution was prepared with a 1:100 ratio in 0.1 M MES buffer (pH 5.5). In order to initiate the crosslinking chemistry, EDC and NHS solutions were added to the antibody mixture, leading to a concentration of 1 mM EDC and 3 mM NHS. The mixture was stirred for 5 minutes and then 1% v/v APTES was added to the solution. The CD34-APTES solution was mixed for 2 hours and further transferred to float-a-lyzer dialysis membranes for purification. The solution was dialyzed for a minimum of six cycles.

(b) Surface Modification of ePTFE Substrates (i) Initial Activation of ePTFE Surfaces Using Oxygen Plasma Prior to modifying the ePTFE surfaces using the two techniques, hydroxyl functional groups were created on their surfaces using an oxygen plasma machine (Herrick Plasma Cleaner, PDC-002, 230 V). ePTFE samples were exposed to high-pressure oxygen plasma for 5 minutes. The hydroxyl groups generated on the ePTFE substrates were used to covalently attach the APTES or CD34-APTES molecules in the next modification steps.

(ii) Creating Anti-CD34 Antibody Functionalized ePTFE Surfaces Using CVD of APTES After removing the hydroxyl functionalized ePTFE substrates from the plasma machine, they were placed in a vacuum desiccator and a droplet of 200 µL of APTES was added on a glass slide and placed beside the ePTFE samples. The vacuum pomp was turned on and after reaching a pressure of −0.085 MPa, the outlet valve was closed and the CVD of the APTES molecules onto the ePTFE samples was initiated. The silanization was carried out for 4 hours at room temperature. Once the silanization step was completed, the APTES functionalized ePTFE substrates were removed from the desiccator and placed in an oven set at 60° C. for 12 hours. After removing the APTES functionalized ePTFE samples from the oven, they were glued to the bottom of the wells of a 96 well plate using a medical grade silicon adhesive (Silbione, Bluestar Silicones, Burlington, ON). Further, the substrates were biofunctionalized with the anti-CD34 antibody using the carbodiimide crosslinker chemistry. Anti-CD34 antibody solution with a concentration of 5 µg/mL in 0.1 M MES buffer (pH 5.5) was prepared and 2 mM EDC and 5 mM NHS was added to the antibody solution in order to initiate the EDC/NHS reaction. The solution was added to the APTES treated ePTFE substrates and the samples were incubated with the antibody solution overnight. After removing the solution, samples were rinsed with PBS in order to remove the physically bonded antibodies from the surface. The CD34 attachment was investigated using a fluorescence microscope (Zeiss Primovert upright fluorescent microscope) and the green fluorescence intensity was quantified using ImageJ. The stability of the anti-CD34 antibody coated surfaces was investigated by washing the surfaces with TBST buffer and incubating the modified substrates with the buffer for 2 weeks. Surfaces were imaged after each washing step and the fluorescence intensity was calculated using ImageJ. Results obtained from the stability experiments were compared with surfaces that were coated with the antibody through physical adsorption.

(iii) Creating Biofunctional ePTFE Surfaces Using APTES Silanized Anti-CD34 Antibody In this technique, oxygen plasma treated ePTFE surfaces were functionalized with APTES treated antibodies. Anti-CD34 antibody was silanized with APTES using the EDC/NHS chemistry. The chemical reaction was carried out in 0.1 M MES buffer (pH 5.5) for 2 hours. Initially, anti-CD34 antibody was added to the MES buffer yielding to a concentration of 5 µg/mL and then 2 mM EDC and 5 mM NHS was added to the solution. In a subsequent step, APTES was added to the mixture (0.5% v/v) and the solution was left stirring at room temperature for 2 h. The solution mixture was transferred to dialysis membranes (molecular weight cut off 3.5-5 kDa) and dialyzed for four to six cycles in order to purify the antibody mixture from non-reacted APTES molecules. Oxygen plasma treated ePTFE substrates were incubated with the purified CD34-APTES solution overnight. After removing the antibody solution, ePTFE substrates were washed to remove non-bonded antibodies from the surface. The CD34 attachment and the stability of the coating was investigated as described above.

(c) Surface Characterization of ePTFE Modified Substrates (i) X-ray Photoelectron Spectroscopy (XPS)

XPS was used to assess the surface chemical composition of the ePTFE surfaces before and after each modification technique. Three ePTFE substrates were subjected to XPS analysis for each condition and means were calculated. XPS spectra were recorded using a Physical Electronics (PHI)

Quantera II spectrometer equipped with an Al anode source for X-ray generation and a quartz crystal monochromator was used to focus the generated X-rays (BioInterface Institute, McMaster University). The monochromatic Al K-α X-ray (1486.7 eV) source was operated at 50 W 15 kV with a system base pressure no higher than $1.0\times10^{-9}$ Torr and an operating5 pressure that did not exceed $2.0\times10^{-8}$ Torr. A pass energy of 280 eV was used to obtain survey spectra and spectra were obtained at 45° take off angles using a dual beam charge compensation system for neutralization. The raw data were analyzed using the instrument software and the atom percentages of carbon, oxygen, fluorine, bismuth, silicon and chlorine were calculated (ii) Contact and Sliding Angle Measurements The contact and sliding angles of the treated and control ePTFE surfaces were measured in order to investigate their lubricant-infused slippery properties before and after each modification step. A Future Digital Scientific OCA20 goniometer (Garden City, NY) was used to measure the water sessile drop contact angles of the substrates. Sliding angles were measured using a digital angle level (ROK, Exeter, UK). Prior to starting the measurements, ePTFE samples were lubricated with PFPP and a 5 µL droplet of deionized water was placed on their surface. The sliding angle was defined as the minimum angle required for droplets to start sliding once the level was tilted. If the droplet failed to slide at angles of 90 degrees or higher, a sliding angle of 90 degrees was assigned to that sample. Measurements were performed in triplicates and the means were calculated.

(iii) Scanning Electron Microscopy (SEM)

SEM was performed on ePTFE samples in order to investigate the endothelial cell adhesion and blood-cell interaction and clot formation on control and modified surfaces. Samples were fixed in 2% glutaraldehyde (2% v/v in 0.1M sodium cacodylate buffer) overnight. The samples were rinsed twice in buffer solution, post-fixed in 1% osmium tetroxide in 0.1M sodium cacodylate buffer for 1 hour and then dehydrated through a graded ethanol series. While the samples were immersed in 100% ethanol, they were placed into wire baskets and transferred to the chamber of a Leica EM CPD300 critical point dryer (Leica Mikrosysteme GmbH, Wien, Austria). The chamber was sealed and then flushed 12 times with liquid $CO_2$. The $CO_2$ filled chamber was heated to 35° C. and the pressure in chamber was increased to above 1100 psi. The gas was vented slowly from the chamber until atmospheric pressure was reached and the samples were dehydrated without surface tension damage. The dried samples were mounted onto SEM stubs with double-sided carbon tape. The samples on stubs were then placed in the chamber of a Polaron Model E5100 sputter coater (Polaron Equipment Ltd., Watford, Hertfordshire) and approximately 4 nm of gold was deposited onto the samples. Samples were then removed from the sputter coater and SEM imaging (JSM- 7000 F) was performed in back-scatter detector mode at 10 kx, 5 kx and 1 kx magnification.

(iv) Thrombin Generation Assay

A fluorogenic thrombin generation assay was used to compare the effect of different modification techniques on thrombin generation. Control and treated ePTFE substrates were cut into 6 mm discs using a biopsy punch (Integra Miltex, Plainsboro, NJ) and glued to the bottom of the uncoated 96 well flat-bottom plates (Evergreen Scientific, Rancho Dominguez, CA) using a medical grade silicon adhesive (Silbione, Bluestar Silicones, Burlington, ON). To wells with or without the ePTFE discs, 80 µL of plasma and 20 µL of 0.02 M HEPES buffer was added. After incubating the plates for 10 minutes at 37 degrees, 100 µL aliquots of 1 mM Z-Gly-Gly-Arg-AMC in HBS containing 25 mM $CaCl_2$ was added to each well. The substrate hydrolysis was monitored using a FlexStation 3 fluorescence plate reader (Molecular Devices, Sunnyvale, CA) at 1 minute intervals for 120 minutes at excitation and emission wavelengths of 360 and 460 nm, respectively, and the emission cut-off filter of 455 nm. Thrombin generation results were analysed using Technothrombin TGA evaluation software (Vienna, Austria) and the assay was calibrated with the Technothrombin TGA CAL SET according to manufacturer's instructions (Technoclone). Peak thrombin (nM), time to peak thrombin (min), lag time to initial thrombin generation (min), the area under the curve or endogenous thrombin potential (ETP, nM.min), and velocity index (nM/min) were determined using the instrument software.

(v) Assessing the Bioactivity of ePTFE Grafts—Endothelial Cell Adhesion and Growth The bioactivity, endothelial cell adhesion and the ability of the surfaces to create an endothelial layer was investigated. Control and anti-CD34 antibody treated ePTFE surfaces were cut into 6 mm disks, a size chosen to cover the bottom of 96-well plates, and glued to the bottom of the wells. To each well, 150 µL of RFP-HUVEC solution with a concentration of $2\times10^5$ cell/mL was added. Prior to adding the cell solution, samples that required lubricant were infiltrated with PFPP for 10 minutes and the excess amount of lubricant was removed before adding the cells. Further, the ePTFE+cell containing plates were placed in an incubator at 37° C. and 5% CO2 for 24 hours. Surfaces were washed with pre-warmed cell media (3×) in order to remove the non-adhered cells, fixed and imaged using an upright fluorescence microscope and SEM. The number of cells/area attached to each substrate and the potency of the surfaces to create an endothelial layer was investigated.

(vi) Blood Clot Formation and Blood Cell Repellency Properties in Human Whole Blood The blood repellency and anti-clotting properties of the control and modified ePTFE surfaces were accessed using re-calcified whole human blood. ePTFE grafts were cut into 7 mm thick rings, pre-weighed and placed around the walls of a 48 well plate, leaving the center of the well unobstructed. Lubricated and non-lubricated ePTFE samples were used as controls. To each well, 500 µL of citrated whole blood was added and further, the blood was re-calcified by adding 500 µL of 1M $CaCl_2$ in HEPES. The grafts were incubated with re-calcified blood for 2 hours at room temperature. The blood clot containing ePTFE grafts were gently removed from the wells briefly blotted on an absorbent bench pad and weighed. The blood clot mass was calculated by subtracting the initial and final weighs of the ePTFE grafts. Further, ePTFE grafts were fixed and subjected to SEM imaging in order to assess the clot adhesion and blood cell repellency properties of the surfaces.

(vii) Statistical Analysis

Data are presented as means±S.D. One-way analysis of variance (ANOVA) followed by post hoc analysis using Tukey's test was performed to assess statistical significance. For all comparisons, P values less than 0.05 were considered statistically significant.

Results (a) Surface Modification of ePTFE Vascular Grafts

Synthetic ePTFE vascular grafts were used for all experiments. Vascular grafts were biofunctionalized using both the conventional technique (creating an APTES-SAM and immobilizing the antibody using EDC/NHS) and the method of the present application using silanized CD34-APTES antibodies. Further, the surfaces from both groups were lubricated using PFPP prior to performing the experiments and the results were compared with non-lubricated biofunctional surfaces and control lubricated and non-lubricated ePTFE substrates.

FIG. 11a shows that in the control experiments, untargeted biospecies attached to unmodified PTFE surfaces and these surfaces do not show anticoagulant or blocking properties. FIG. 11b shows that when lubricating the PTFE control substrates, a lubricant-infused slippery surface can be obtained that both prevents specific and non-specific adhesion of cells and biospecies. The PTFE surfaces are functionalized using the conventional technique were the substrate is completely coated with APTES (the coupling agent) and further, the CD34 antibody is immobilized on the surface. FIG. 11c shows that these surfaces promote endothelial cell adhesion but do not have blocking properties. ePTFE surfaces are oxygen plasma treated and functionalized with CD34-APTES silanized antibodies. FIG. 11d shows that the biofunctional lubricant-infused surfaces prevent non-specific adhesion and promote specific binding of endothelial cells.

(b) Surface Chemical Composition

XPS was performed on control, $O_2$ plasma treated and APTES-CVD treated ePTFE surfaces in order to investigate their surface chemical properties and the differences in the fluorine atom % after each modification step (FIGS. 12a and 12b). The fluorine atom % decreased after oxygen plasma treatment but the difference was not significant when comparing the results with control samples. APTES treated ePTFE surfaces had a significantly lower atom % of fluorine present on their surface (17.1±6.7%) compared with control and $O_2$ treated substrates (66.7±0.6 and 50.8±2.5 respectively). The F/C ratio was significantly lower in APTES treated surfaces (0.4±0.2) compared with control (2.0±0.1) and $O_2$ treated samples (1.2±0.1). The oxygen atom % was significantly higher in oxygen plasma treated surfaces compared with control ePTFE substrates (7.7±0.9 and 0.1±0.1% respectively).

FIGS. 12a and 12b show that after oxygen plasma treating the ePTFE graft, the atom % of the oxygen increased, which indicates the presence of hydroxyl functional groups on ePTFE grafts after oxygen plasma treatment. No significant difference was seen in the F atom % when comparing the results with the control ePTFE grafts. In contrast, when adding the APTES monolayer, the amount of surface F significantly decreased. The atom % of N and Si confirm the presence of APTES on the surface.

(c) Sliding and Contact Angle Measurements

The slippery properties of the control and lubricant-infused treated surfaces were determined using contact and sliding angle measurements (FIGS. 12c and 12d). All samples, except for control-NL surfaces were lubricated prior to performing the sliding angle measurements. The droplet did not slide on non-lubricated control ePTFE surfaces. However, after infiltrating the ePTFE substrates with the PFPP lubricant, sliding angles decreased significantly and the surfaces exhibited an average sliding angle of 14.2±1.9 degrees (FIG. 12c). After oxygen plasma treating the ePTFE substrates and introducing hydroxyl functional groups onto their surfaces, the sliding angles slightly increased (26.5±5.1 degrees). Similar to non-lubricated control ePTFE samples, the droplet did not slide on lubricant infused APTES-CVD surfaces and these surfaces did not show slippery properties (FIG. 12c).

In the contact angle measurements, both control and oxygen plasma treated surfaces exhibited hydrophobic properties and had static contact angles higher than 100 degrees (115.4±2.8 and 105.2±7.1 respectively). In contrast, APTES-CVD treated surfaces, were hydrophilic and exhibited an average static contact angle of 77.4±9.2 degrees (FIG. 12d).

(d) Surface Topography and Presence of Anti-CD34 Antibody—Fluorescence and SEM Images Control, APTES-CVD+CD34 and CD34-APTES treated surfaces were imaged using fluorescence microscopy and SEM in order to investigate the presence and stability of the anti-CD34 antibody coating and to evaluate the surface topography after each modification step (FIGS. 12e and 12f). The fluorescence images revealed the presence and stability of the anti-CD34 antibody on both APTES-CVD+CD34 and CD34-APTES treated samples after the multiple washing steps. No significant decrease was seen in the fluorescence intensity after incubating the samples in 1% TBST buffer for 2 weeks. However, there was a significant decrease in the fluorescence intensity on samples coated with the antibody through physical adsorption (FIG. 12f). When looking at the SEM images, control, APTES-CVD+CD34, CD34-APTES treated surfaces showed similar surface topography and ePTFE structure and no visible difference was seen between treated surfaces and control ePTFE samples (FIG. 12e).

(e) Effect of Surface Modification on ePTFE-induced Thrombin Generation

Thrombin generation was performed in the absence (background) or presence of lubricated and non-lubricated control and CD34-treated ePTFE samples in order to investigate the anti-thrombogenicity of the biofunctional and/or lubricant-infused surfaces and the efficiency of the developed coating in attenuating thrombin generation (FIGS. 13a and 13b). Lubricant-infused ePTFE substrates, functionalized with the developed silanized anti-CD34 antibody (CD34-APTES+L) significantly (P<0.001) prolonged the lag time and time to peak thrombin and significantly reduced (P<0.001) peak thrombin, velocity index and ETP compared with non-modified control, APTES-CVD+CD34 and non-lubricated CD34-APTES ePTFE surfaces. Biofunctional lubricant-infused CD34-APTES+L surfaces suppressed thrombin generation to a similar extent as the background and no significant difference was seen in the thrombin generation parameters when comparing these two groups. In contrast, all other treated groups and control samples significantly induced thrombin generation compared with the background.

The potency of the lubricant layer in reducing thrombin generation was observed when comparing the lubricated and non-lubricated results in control and CD34-APTES treated groups, something that was not evident in APTES-CVD+CD34 treated samples. Control+L samples significantly prolonged the lag time and reduced peak thrombin and velocity index compared with Control-NL samples. However, no significant difference was seen when comparing the thrombin generation parameters from APTES-CVD+CD34+L with APTES-CVD+CD34-NL treated samples (FIGS. 13a and 13b).

In addition to the lubricant, the presence of the anti-CD34 antibody with/without the lubricant suppressed thrombin generation compared with Control-NL samples. Similar to the CD34-APTES+L samples, other anti-CD34 antibody functionalized ePTFE substrates coated using both treatment techniques significantly reduced peak thrombin and velocity index and significantly prolonged the lag time and time to peak thrombin when compared with Control-NL samples (FIGS. 13a and 13b).

FIGS. 13a and 13b show that CD34-APTES+L treated surfaces significantly suppressed thrombin generation compared to control and other treated groups. No significant difference was seen when comparing the results with blank plates. *P<0.001 and ‖P<0.05 compared with CD34-APTES+L. ‡P<0.001 and ˆP<0.05 compared with Blank plate. ¥P<0.008 and θP<0.05 compared with Control+L. °P<0.005 compared with APTES-CVD+CD34+L, NL and CD34-APTES-NL.

(f) Bioactivity and Endothelialization of the Lubricant Infused, Anti-CD34 Antibody Treated ePTFE Surfaces The bioactivity of the anti-CD34 antibody coated surfaces and their ability to promote cell adhesion and endothelialization was investigated by incubating these surfaces with RFP-HUVECs and the results were compared with lubricated and non-lubricated control ePTFE samples. As seen in FIG. 14, Control-L samples blocked the ePTFE surfaces and significantly inhibited cell adhesion and growth compared with Control-NL samples (0.8±0.5 and 9.6±1.6 cell/mm$^2$ respectively). Control-NL ePTFE surfaces showed significantly less cell adhesion compared with the anti-CD34 functionalized surfaces. As seen in the fluorescence and SEM images (FIGS. 14a and 14b), cells were individually adhered to the Control-NL surfaces and had a spherical morphology, while cells were elongated and well spread on anti-CD34 functionalized surfaces. In addition, in APTES-CVD+CD34+L and CD34-APTES+L samples, the presence of the lubricant layer resulted in higher cell-cell interaction compared with non-lubricated surfaces and CD34-APTES+L samples showed higher degrees of endothelialization compared with APTES-CVD+CD34+L and non-lubricated anti-CD34 functionalized surfaces.

As shown in FIG. 14c, cell count per mm$^2$ was significantly lower in Control-L and Control-NL when compared to CD34 treated surfaces (*P<0.05). Control-L samples had significantly less cells compared to Control-NL samples as well. Bars show the means±SD of at least three samples.

For long term cell adhesion results, ePTFE grafts were incubated with RFP-HUVECs for 4 days and endothelial cell adhesion and the formation of a confluent endothelial layer, cell phenotype and cytocompatibility of the treated surfaces was investigated and the results were compared with control surfaces. The positive immunofluorescence staining for Alexa fluor 488-conjugated VEcadherin (green) confirm the HUVEC phenotype for adherent cells. In contrast to control and lubricant-infused ePTFE surfaces, the optimized CD34 functionalized lubricant-infused surfaces promoted cell adhesion and the formation of a confluent endothelial layer was observed on these surfaces. The ePTFE+L samples inhibited the non-specific binding of cells and had significantly less adherent cells after 4 days compared to other treated substrates.

(d) Clot Formation and Blood Cell Adhesion on Modified and Control ePTFE Surfaces The anticlotting and blood cell repellency properties of the coated surfaces was investigated using re-calcified whole human blood (FIG. 15). Upon visual investigation and post-weighing of the samples, CD34-APTES+L samples had the lowest amount of blood clot adhered to their surfaces and they remained relatively clean compared with control and other treated groups (FIGS. 15a and 15b). In addition, when looking at the SEM images, the developed biofunctional lubricant-infused CD34-APTES surfaces had significantly less protein and blood cell adhesion compared with other groups (FIG. 15c). In contrast, Control-NL samples had significantly larger blood clot masses adhered to their surfaces compared with Control-L and biofunctional CD34 treated samples and the SEM images revealed the formation of a dense clot layer and a large amount of blood cells adhered on these surfaces. Similar to the results obtained from the thrombin generation assays, the addition of the lubricant layer did not significantly affect the clot formation and cell adhesion on APTES-CVD+CD34 treated samples and no significant difference was seen between the clot mass and blood cell adhesion in APTES-CVD+CD34+L and NL groups. However, when comparing the lubricated and non-lubricated samples from the control and CD34-APTES treated groups, adding the lubricant significantly decreased the clot mass, protein, and blood cell adhesion on these surfaces. In addition to the lubricant, the presence of the anti-CD34 antibody had a significant effect on blood clot and cell adhesion. Samples treated with the antibody using both modification techniques had significantly less blood clot and blood cells adhered to their surfaces when compared to Control-NL samples (FIG. 15).

Discussion

Preventing non-specific adhesion of biomolecules and concurrently stimulating endothelialization are two features that are desirable for the optimal performance of synthetic vascular grafts [35]. Biofunctional lubricant-infused ePTFE grafts that prevent thrombin generation and clot formation and promote endothelial cell adhesion have been prepared and assessed using methods of the present application. In this method, ePTFE substrates were biofunctionalized with a method using APTES silanized anti-CD34 antibodies and lubricated with a fluorocarbon-based lubricant, creating a bio-targeting interface with excellent repellency properties. This surface modification method preserved the surface chemical properties of the ePTFE substrate, allowing the lubricant layer to stabilize on the ePTFE fluorosilinated surface and as a result creating a stable, lubricant-infused layer.

When looking at the results obtained from the XPS measurements, by coating the ePTFE layer with an APTES monolayer, the surface fluorine atom % and the F/C ratio decreased. The optimal functioning of slippery lubricant-infused surfaces relies on the strong fluorine-fluorine interactions induced between the liquid lubricant and the fluorine molecules present on the substrate [36]. Coating the ePTFE layer with a SAM of APTES, prevented the intermolecular interaction between the ePTFE layer and with the lubricant, therefore, these surfaces did not show lubricant-infused slippery properties. In contrast, XPS results and sliding and contact angle measurements confirm that ePTFE control substrates retain their lubricant-infused slippery properties after inducing hydroxyl functional groups on their surfaces using oxygen plasma treatment. The slight increase in the sliding angle and decrease in the contact angle after plasma treating the ePTFE substrates could be attributed to the presence of hydroxyl groups on the ePTFE surface after oxygen plasma. Hydroxyl groups are strongly hydrophilic and polar functional groups and their presence affects the physical properties (sliding and contact angle properties) of the substrate [37].

The results obtained from the thrombin generation assay and blood clotting experiments, demonstrate the efficacy of the CD34-APTES+L treated surfaces in significantly decreasing thrombin generation and clot formation on ePTFE grafts. The combination of CD34-APTES immobilization and adding the lubricant layer onto the ePTFE surfaces had superior performance compared with control and other treated ePTFE surfaces. In addition, CD34-APTES+L surfaces suppressed thrombin generation to the same extend as the background (blank plate), which did not contain any ePTFE samples. Omniphobic lubricant-infused slippery surfaces are best known for their outstanding ability in preventing non-specific adhesion of biomolecules and cells [36], [20], [21]. Further, lubricant-infused control surfaces exhibited similar characteristics by significantly decreasing thrombin generation and non-specific adhesion of HUVECs compared with non-lubricated control ePTFE substrates. In addition to the lubricant layer, the anti-thrombotic properties of the anti-CD34 antibody cannot be denied, as ePTFE substrates treated with both CD34-APTES and the conventional immobilization technique significantly reduced thrombin generation and blood adhesion compared with non-modified Control-NL surfaces. This phenomenon has also been observed in other studies that have used anti-CD34 antibody as an endothelial cell specific marker to increase endothelial cell capture and adhesion [38], [39]-[41]. These studies report increased hemocompatibility and less platelet adhesion on modified surfaces coated with anti-CD34 antibody biomarker. Further, clinical investigations conducted on implanted bioengineered stents, coated with anti-CD34 antibody have shown that endothelial capturing stents are safe and no stent thrombosis was observed 30 days or 6 months after implantation [42].

Similar to previously reported studies which used anti-CD34 as an endothelial specific cell marker [43], [9], [44], the anti-CD34 antibody coated ePTFE surfaces significantly increased endothelial cell capture and adhesion compared to non-coated substrates. As seen in the fluorescence and SEM images, lubricated biofunctionalized surfaces exhibited a higher degree of cell-cell interaction and endothelial layer formation compared to non-lubricated surfaces. This indicates that the anti-CD34 antibodies remain functional and accessible after adding the lubricant layer. Control lubricant-infused ePTFE samples exhibited excellent blocking properties by significantly decreasing endothelial cell adhesion compared with Control-NL samples. This confirms the ability of these surfaces to prevent non-specific adhesion, similar to previously reported ePTFE lubricant-infused substrates [45], [20].

Example 3

Fluorosilinated Biofunctional Lubricant-infused PET Grafts with Built-in Functional Groups Prevent Non-specific Adhesion and Promote Endothelialization Materials Alexa Fluor 488 conjugated mouse anti-human CD34 antibody and trypsin-EDTA (0.25%) were purchased from ThermoFisher Scientific (Massachusetts, United States). Trichloro (1H, 1H, 2H, 2H-perfluorooctyl) silane (TPFS), perfluoroperhydrophenanthrene (PFPP), 3-aminopropyltriethoxy-silane (APTES), N-(3-Dimethylaminopropyl)-N'-ethylcarbodiimide (EDC), N-Hydroxysuccinimide (NHS), 2-(N-Morpholino) ethanesulfonic acid (MES), spectra-por float-a-lyzer G2 dialysis tubes were purchased from Sigma-Aldrich (Oakville, Canada). Red Fluorescent Protein Expressing Human Umbilical Vein Endothelial Cells (RFP-HUVEC) were generously donated by Dr. P. Ravi Selvaganapathy's lab at McMaster University. Cell media kit (EGM-2 BelletKit) and trypsin neutralizing agent where purchased from Cedarlane (Burlington, Canada). The thrombin-directed fluorescent substrate, Z-Gly-Gly-Arg-AMC, was purchased from Bachem (Bubendorf, Switzerland). Dacron (Polyethylene terephthalate, PET) vascular grafts were kindly provided by Hamilton Health Sciences (Hamilton, ON). Whole human blood and pooled citrated plasma was generated from blood samples collected from healthy donors. A signed written consent was collected from donors and all procedures were approved by the McMaster University Research Ethics Board.

Methods (a) Surface Modification of PET Substrates (i) Initial activation of PET surfaces using oxygen plasma:

Prior to functionalizing the PET surfaces with TPFS and creating a TPFS-SEM, hydroxyl functional groups were generated on their surfaces using oxygen plasma (Herrick Plasma Cleaner, PDC-002, 230 V). PET samples were cut into appropriate disc sizes and exposed to high-pressure oxygen plasma for 2 minutes.

(ii) Preparation of Fluorosilanized PET Surfaces Using CVD:

After removing the oxygen plasma-treated PET discs from the plasma cleaner, they were immediately placed in a desiccator connected to a vacuum pump and in a separate petri dish, 400 µL of TPFS was added and placed beside the PET substrates. The vacuum pump was turned on and once a pressure of −0.085 MPa was achieved, the exit valve was closed and CVD process was initiated. The silanization reaction was carried out for about 5 hours at room temperature. After the CVD step, PET surfaces were removed from the desiccator and placed in an oven at 60° C. overnight in order to complete the condensation step. After removing the samples from the oven, they were placed under vacuum for 30 mins with an open exit valve to ensure removal of non-bonded silanes from the surface.

(iii) Post Plasma Treatment of TPFS Functionalized PET Surfaces:

After removing the PET samples from the oven, substrates were exposed to a secondary oxygen plasma treatment for 30 seconds in order to partially etch the fluorine SEM layer and to create hydroxyl functional groups on the fluorosilanized surface. The hydroxyl functionalized fluorosilinated surfaces were then removed and glued to the bottom of the wells of a 96 well plate using a medical grade silicon adhesive (Silbione, Bluestar Silicones, Burlington, ON). PET-TPFS surfaces with no secondary plasma treatment were used as controls. These surfaces were lubricated prior to preforming further experiments.

(iv) Creating Biofunctional PET Surfaces Using APTES Silanized Anti-CD34 Antibody (TPFS+CD34-APTES):

Prior to adding anti-CD34 antibody to the PET substrates, the antibody was silanized with APTES using EDC/NHS chemistry. The chemical reaction was carried out in 0.1 M MES buffer (pH 5.5) for 2 hours. Initially, anti-CD34 antibody was added to the MES buffer yielding to a concentration of 5 µg/mL and then 2 mM EDC and 5 mM NHS was added to the solution. In a subsequent step, APTES was added to the mixture (0.5% v/v) and the solution was left stirring at room temperature for 2 h. The solution mixture was transferred to dialysis membranes (molecular weight cut off 3.5-5 kDa) and dialyzed for four to six cycles in order to purify the antibody mixture from non-reacted APTES molecules. Fluorosilanized, hydroxyl functionalized PET substrates were incubated with the purified CD34-APTES solution overnight in order to obtain CD34-APTES functionalized PET-TPFS surfaces. After removing the antibody solution, PET substrates were washed to remove non-bonded antibodies from the surface.

(v) Surface Characterization of PET Modified Substrates

X-ray Photoelectron Spectroscopy (XPS):

XPS was used to assess the surface chemical composition of the PET surfaces before and after each modification technique. Three PET substrates were subjected to XPS analysis for each condition and means were calculated. XPS spectra were recorded using a Physical Electronics (PHI) Quantera II spectrometer equipped with an Al anode source for X-ray generation and a quartz crystal monochromator was used to focus the generated X-rays (BioInterface Institute, McMaster University). The monochromatic Al K-α X-ray (1486.7 eV) source was operated at 50 W 15 kV with a system base pressure no higher than $1.0 \times 10-9$ Torr and an operating pressure that did not exceed $2.0 \times 10-8$ Torr. A pass energy of 280 eV was used to obtain survey spectra and spectra were obtained at 45° take off angles using a dual beam charge compensation system for neutralization. The raw data were analyzed using the instrument software and the atom percentages of carbon, oxygen, fluorine, bismuth, silicon and chlorine were calculated.

As shown in FIG. 18a, the presence of fluorine after CVD treating the substrates with TPFS, confirms the formation of the fluorosilane self-assembled monolayer (SEM) on the PET surfaces. After conducting the secondary oxygen plasma treatment on the fluorosilanized surfaces, the atom% of fluorine decreased and the atom% of oxygen increased, which confirms the partial removal of the fluorosilane layer and formation of the hydroxyl groups on the surface.

Contact and Sliding Angle Measurements:

The contact and sliding angles of the control-PET, oxygen plasma treated (PET-TPFS+plasma) and fluorosilinated biofunctionalized PET surfaces (TPFS+CD34-APTES) were measured in order to investigate their lubricant-infused slippery properties before and after each modification step. A Future Digital Scientific OCA20 goniometer (Garden City, NY) was used to measure the water sessile drop contact angles of the substrates. After placing the droplet on the control and modified PET surfaces, images were taken in 5 second intervals in order to study the water repellency properties of the PET modified surfaces and their ability to prevent the water droplet from getting adsorbed onto the surface. Sliding angles were measured using a digital angle level (ROK, Exeter, UK). Prior to starting the measurements, PET samples were lubricated with PFPP and a 5 µL droplet of deionized water was placed on their surface. The sliding angle was defined as the minimum angle required for droplets to start sliding once the level was tilted. If the droplet failed to slide at angles of 90 degrees or higher, a sliding angle of 90 degrees was assigned to that sample. Measurements were performed in triplicates and the means were calculated.

FIG. 18b shows sliding and contact angle measurements on control, lubricant infused and BLIS confirming the slippery properties of the substrates. Samples treated with TPFS, had significantly higher contact angles compared to control PET surfaces. In water-substrate interaction studies, FIG. 18c shows that in contrast to the control PET surfaces, the water droplet was not absorbed onto the surfaces of PET-TPFS, PET-TPFS+$O_2$ and TPFS+CD34-APTES substrates.

Scanning Electron Microscopy (SEM):

SEM was performed on PET samples in order to investigate the blood-cell interaction and clot formation on control and modified surfaces. Samples were fixed in 2% glutaraldehyde (2% v/v in 0.1M sodium cacodylate buffer) overnight. The samples were rinsed twice in buffer solution, post-fixed in 1% osmium tetroxide in 0.1M sodium cacodylate buffer for 1 hour and then dehydrated through a graded ethanol series. While the samples were immersed in 100% ethanol, they were placed into wire baskets and transferred to the chamber of a Leica EM CPD300 critical point dryer (Leica Mikrosysteme GmbH, Wien, Austria). The chamber was sealed and then flushed 12 times with liquid CO2. The CO2 filled chamber was heated to 35° C. and the pressure in chamber was increased to above 1100 psi. The gas was vented slowly from the chamber until atmospheric pressure was reached and the samples were dehydrated without surface tension damage. The dried samples were mounted onto SEM stubs with double-sided carbon tape. The samples on stubs were then placed in the chamber of a Polaron Model E5100 sputter coater (Polaron Equipment Ltd., Watford, Hertfordshire) and approximately 4 nm of gold was deposited onto the samples. Samples were then removed from the sputter coater and SEM imaging (JSM-7000 F) was performed at 10 kx, 5 kx and 1 kx magnification.

Thrombin Generation Assay

A fluorogenic thrombin generation assay was used to compare the effect of different modification techniques on thrombin generation. Control and treated PET substrates were cut into 6 mm discs using a biopsy punch (Integra Miltex, Plainsboro, NJ) and glued to the bottom of the uncoated 96 well flat-bottom plates (Evergreen Scientific, Rancho Dominguez, CA) using a medical grade silicon adhesive (Silbione, Bluestar Silicones, Burlington, ON). To wells with or without the PET discs, 80 µL of plasma and 20 µL of 0.02 M HEPES buffer was added. After incubating the plates for 10 minutes at 37 degrees, 100 µL aliquots of 1 mM Z-Gly-Gly-Arg-AMC in HBS containing 25 mM CaCl2 was added to each well. The substrate hydrolysis was monitored using a FlexStation 3 fluorescence plate reader (Molecular Devices, Sunnyvale, CA) at 1 minute intervals for 120 minutes at excitation and emission wavelengths of 360 and 460 nm, respectively, and the emission cut-off filter of 455 nm. Thrombin generation results were analysed using Technothrombin TGA evaluation software (Vienna, Austria) and the assay was calibrated with the Technothrombin TGA CAL SET according to manufacturer's instructions (Technoclone). Peak thrombin (nM), time to peak thrombin (min), lag time to initial thrombin generation (min), the area under the curve or endogenous thrombin potential (ETP, nM.min), and velocity index (nM/min) were determined using the instrument software.

FIG. 19 shows TPFS+CD34-APTES+L treated surfaces significantly suppressed thrombin generation compared to control PET and lubricant-infused surfaces. Values represent means±SD of at least 10 samples.

Assessing the Bioactivity of PET Grafts—Endothelial Cell Adhesion and Growth

The bioactivity, endothelial cell adhesion and the ability of the surfaces to capture endothelial cells from a complex biological solution such as blood was investigated. Control, PET-TPFS and anti-CD34 antibody treated PET surfaces were cut into 6 mm disks, a size chosen to cover the bottom of 96-well plates, and glued to the bottom of the wells. To each well, 150 µL of RFP-HUVEC+blood solution with a concentration of $2 \times 10^5$ cell/mL was added. Prior to adding the cell solution, samples that required lubricant were infiltrated with PFPP for 10 minutes and the excess amount of lubricant was removed before adding the cells. Further, the cell containing plates were placed in an incubator at 37° C. and 5% CO2 for 4 days. Further, surfaces were washed with pre-warmed cell media (3×) in order to remove the non-adhered cells, fixed using 4% formalin in PBS and imaged using an upright fluorescence microscope. The number of cells/area attached to each substrate and the potency of the surfaces to create an endothelial layer was investigated.

FIG. 20 shows TPFS+CD34-APTES+L surfaces showed excellent cell targeted binding properties and were able to capture endothelial cells from blood. In contrast, PET-TPFS+L surfaces completely blocked the surfaces and minimum cell attachment was observed on these surfaces. Control PET surfaces with no biofunctionality had significantly more cells adhered to their surfaces compared to PET-TPFS+L samples.

Blood Clot Formation and Blood Cell Repellency Properties in Human Whole Blood

The blood repellency and anti-clotting properties of the control and modified PET surfaces were accessed using re-calcified whole human blood. PET grafts were cut into 6 mm in diameter discs and placed at the bottom of the wells of a 96 well plate. Lubricated and non-lubricated PET samples were used as controls. To each well, 100 µL of citrated whole blood was added and further, the blood was re-calcified by adding 100 µL of 1M $CaCl_2$ in HEPES. The PET discs were incubated with re-calcified blood for 2 hours at room temperature. PET grafts were gently removed from the wells briefly blotted on an absorbent bench pad and fixed in 4% formalin for 20 min. Further, PET grafts were subjected to SEM imaging in order to assess the clot adhesion and blood cell repellency properties of the surfaces.

FIG. 19c specifically shows that the optimized BLIS and Lubricant infused surfaces (LIS) significantly reduced clot formation and blood cell adhesion compared to unmodified control substrates.

While the present application has been described with reference to examples, it is to be understood that the scope of the claims should not be limited by the embodiments set forth in the examples, but should be given the broadest interpretation consistent with the description as a whole.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

FULL CITATIONS FOR DOCUMENTS REFERRED TO IN THE APPLICATION

[1] D. G. Castner and B. D. Ratner, Biomedical surface science: Foundations to frontiers, vol. 500, no. 1-3. 2002.

[2] F. Rusmini, Z. Zhong, and J. Feijen, "Protein immobilization strategies for protein biochips," Biomacromolecules, vol. 8, no. 6, pp. 1775-1789, 2007.

[3] J. E. Gautrot, W. T. S. Huck, M. Welch, and M. Ramstedt, "Protein-resistant NTA-functionalized polymer brushes for selective and stable immobilization of histidine-tagged proteins," ACS Appl. Mater. Interfaces, vol. 2, no. 1, pp. 193-202, 2010.

[4] C. Y. K. Lung and J. P. Matinlinna, "Aspects of silane coupling agents and surface conditioning in dentistry: An overview," Dent. Mater., vol. 28, no. 5, pp. 467-477, 2012.

[5] G. Camci-Unal, H. Aubin, A. F. Ahari, H. Bae, J. W. Nichol, and A. Khademhosseini, "Surface-modified hyaluronic acid hydrogels to capture endothelial progenitor cells.," Soft Matter, vol. 6, no. 20, pp. 5120-5126, 2010.

[6] T. F. Didar, A. M. Foudeh, and M. Tabrizian, "Patterning multiplex protein microarrays in a single microfluidic channel," Anal. Chem., vol. 84, no. 2, pp. 1012-1018, 2012.

[7] M. Qin, S. Hou, L. Wang, X. Feng, R. Wang, Y. Yang, C. Wang, L. Yu, B. Shao, and M. Qiao, "Two methods for glass surface modification and their application in protein immobilization," Colloids Surfaces B Biointerfaces, vol. 60, no. 2, pp. 243-249, 2007.

[8] Q. L. Li, N. Huang, C. Chen, J. L. Chen, K. Q. Xiong, J. Y. Chen, T. X. You, J. Jin, and X. Liang, "Oriented immobilization of anti-CD34 antibody on titanium surface for self-endothelialization induction," J. Biomed. Mater. Res.—Part A, vol. 94, no. 4, pp. 1283-1293, 2010.

[9] J. Chen, J. Cao, J. Wang, M. F. Maitz, L. Guo, Y. Zhao, Q. Li, K. Xiong, and N. Huang, "Biofunctionalization of titanium with PEG and anti-CD34 for hemocompatibility and stimulated endothelialization," J. Colloid Interface Sci., vol. 368, no. 1, pp. 636-647, 2012.

[10] Y. L. Jeyachandran, E. Mielczarski, B. Rai, and J. A. Mielczarski, "Quantitative and qualitative evaluation of adsorption/desorption of bovine serum albumin on hydrophilic and hydrophobic surfaces," Langmuir, vol. 25, no. 19, pp. 11614-11620, 2009.

[11] A. S. Anderson, A. M. Dattelbaum, G. A. Montano, D. N. Price, J. G. Schmidt, J. S. Martinez, W. K. Grace, K. M. Grace, and B. I. Swanson, "Functional PEG-modified thin films for biological detection," Langmuir, vol. 24, no. 5, pp. 2240-2247, 2008.

[12] W.-B. Tsai, Y.-H. Chen, and H.-W. Chien, "Collaborative Cell-Resistant Properties of Polyelectrolyte Multilayer Films and Surface PEGylation on Reducing Cell Adhesion to Cytophilic Surfaces," J. Biomater. Sci. Ed., vol. 20, no. 11, pp. 1611-1628, 2009.

[13] Y. Liu and J. Yu, "Oriented immobilization of proteins on solid supports for use in biosensors and biochips: a review," Microchim. Acta, vol. 183, no. 1, pp. 1-19, 2016.

[14] J. Kim, J. Cho, P. M. Seidler, N. E. Kurland, and V. K. Yadavalli, "Investigations of chemical modifications of amino-terminated organic films on silicon substrates and controlled protein immobilization," Langmuir, vol. 26, no. 4, pp. 2599-2608, 2010.

[15] J. I. Rotmans, J. M. M. Heyligers, H. J. M. Verhagen, E. Velema, M. M. Nagtegaal, D. P. V De Kleijn, F. G. De Groot, E. S. G. Stroes, and G. Pasterkamp, "In vivo cell seeding with anti-CD34 antibodies successfully accelerates endothelialization but stimulates intimal hyperplasia in porcine arteriovenous expanded polytetrafluoroethylene grafts," Circulation, vol. 112, no. 1, pp. 12-18, 2005.

[16] G. Festag, A. Steinbruck, A. Wolff, A. Csaki, R. Miler, and W. Fritzsche, "Optimization of gold nanoparticle-based DNA detection for microarrays," J. Fluoresc., vol. 15, no. 2, pp. 161-170, 2005.

[17] Y. Wu, C. Chen, and S. Liu, "Enzyme-functionalized silica nanoparticles as sensitive labels in biosensing," Anal. Chem., vol. 81, no. 4, pp. 1600-1607, 2009.

[18] A. Gang, G. Gabernet, L. D. Renner, L. Baraban, and G. Cuniberti, "A simple two-step silane-based (bio-) receptor molecule immobilization without additional binding site passivation," RSC Adv., vol. 5, no. 45, pp. 35631-35634, 2015.

[19] D. Kim and A. E. Herr, "Protein immobilization techniques for microfluidic assays," Biomicrofluidics, vol. 7, no. 4, pp. 1-47, 2013.

[20] D. C. Leslie, A. Waterhouse, J. B. Berthet, T. M. Valentin, A. L. Watters, A. Jain, P. Kim, B. D. Hatton, A. Nedder, K. Donovan, E. H. Super, C. Howell, C. P. Johnson, T. L. Vu, D. E. Bolgen, S. Rifai, A. R. Hansen, M. Aizenberg, M. Super, J. Aizenberg, and D. E. lngber, "A bioinspired omniphobic surface coating on medical

[21] T.-S. Wong, S. H. Kang, S. K. Y. Tang, E. J. Smythe, B. D. Hatton, A. Grinthal, and J. Aizenberg, "Bioinspired self-repairing slippery surfaces with pressure-stable omniphobicity.," Nature, vol. 477, no. 7365, pp. 443-7, 2011.

[22] D. J. Kim, J. M. Lee, J. G. Park, and B. G. Chung, "A self-assembled monolayer-based micropatterned array for controlling cell adhesion and protein adsorption," Biotechnol. Bioeng., vol. 108, no. 5, pp. 1194-1202, 2011.

[23] P. Filippini, G. Rainaldi, A. Ferrante, B. Mecheri, G. Gabrielli, M. Bombace, P. L. Indovina, and M. T. Santini, "Modulation of osteosarcoma cell growth and differentiation by silane-modified surfaces," J. Biomed. Mater. Res., vol. 55, no. 3, pp. 338-349, 2001.

[24] K. Awsiuk, A. Bernasik, M. Kitsara, A. Budkowski, P. Petrou, S. Kakabakos, S. Prauzner-Bechcicki, J. Rysz, and I. Raptis, "Spectroscopic and microscopic characterization of biosensor surfaces with protein/amino-organosilane/silicon structure," Colloids Surfaces B Biointerfaces, vol. 90, no. 1, pp. 159-168, 2012.

[25] K. Awsiuk, A. Budkowski, A. Psarouli, P. Petrou, A. Bernasik, S. Kakabakos, J. Rysz, and I. Raptis, "Protein adsorption and covalent bonding to silicon nitride surfaces modified with organo-silanes: Comparison using AFM, angle-resolved XPS and multivariate ToF-SIMS analysis," Colloids Surfaces B Biointerfaces, vol. 110, pp. 217-224, 2013.

[26] L. S. Jang and H. J. Liu, "Fabrication of protein chips based on 3-aminopropyltriethoxysilane as a monolayer," Biomed. Microdevices, vol. 11, no. 2, pp. 331-338, 2009.

[27] R. S. Smith, Z. Zhang, M. Bouchard, J. Li, H. S. Lapp, G. R. Brotske, D. L. Lucchino, D. Weaver, L. A. Roth, A. Coury, J. Biggerstaff, S. Sukavaneshvar, R. Langer, and C. Loose, "Vascular Catheters with a Nonleaching Poly-Sulfobetaine Surface Modification Reduce Thrombus Formation and Microbial Attachment," Sci. Transl. Med., vol. 4, no. 153, p. 153ra132-153ra132, 2012.

[28] J. M. Harris and R. B. Chess, "Effect of pegylation on pharmaceuticals.," Nat. Rev. Drug Discov., vol. 2, no. 3, pp. 214-221, 2003.

[29] I. Sotiri, J. C. Overton, A. Waterhouse, and C. Howell, "Immobilized liquid layers: a new approach to anti-adhesion surface for medical applications.," Exp. Biol. Med., vol. in press, pp. 1-10, 2016.

[30] C. Howell, T. L. Vu, C. P. Johnson, X. Hou, O. Ahanotu, J. Alvarenga, D. C. Leslie, O. Uzun, A. Waterhouse, P. Kim, M. Super, M. Aizenberg, D. E. lngber, and J. Aizenberg, "Stability of surface-immobilized lubricant interfaces under flow," Chem. Mater., vol. 27, no. 5, pp. 1792-1800, 2015.

[31] S. P. Pujari, L. Scheres, A. T. M. Marcelis, and H. Zuilhof, "Covalent surface modification of oxide surfaces," Angew. Chemie—Int. Ed., vol. 53, no. 25, pp. 6322-6356, 2014.

[32] C. Haensch, S. Hoeppener, and U. S. Schubert, "Chemical modification of self-assembled silane based monolayers by surface reactions," Chem. Soc. Rev., vol. 39, no. 6, p. 2323, 2010.

[33] C. A. Kretz, K. K. Cuddy, A. R. Stafford, J. C. Fredenburgh, R. Roberts, and J. I. Weitz, "HD1, a thrombin- and prothrombin-binding DNA aptamer, inhibits thrombin generation by attenuating prothrombin activation and thrombin feedback reactions," Thromb. Haemost., vol. 103, no. 1, pp. 83-93, 2010.

[34] J. W. Yau, A. R. Stafford, P. Liao, J. C. Fredenburgh, R. Roberts, and J. I. Weitz, "Mechanism of catheter thrombosis: Comparison of the antithrombotic activities of fondaparinux, enoxaparin, and heparin in vitro and in vivo," Blood, vol. 118, no. 25, pp. 6667-6674, 2011.

[35] S. Lu, P. Zhang, X. Sun, F. Gong, S. Yang, L. Shen, Z. Huang, and C. Wang, "Synthetic ePTFE grafts coated with an anti-CD133 antibody-functionalized heparin/collagen multilayer with rapid in vivo endothelialization properties," ACS Appl. Mater. Interfaces, vol. 5, no. 15, pp. 7360-7369, 2013.

[36] M. Badv, I. H. Jaffer, J. I. Weitz, and T. F. Didar, "An omniphobic lubricant-infused coating produced by chemical vapor deposition of hydrophobic organosilanes attenuates clotting on catheter surfaces," Sci. Rep., vol. 7, no. 1, p. 11639, 2017.

[37] H. H. Chien, K. J. Ma, C. H. Kuo, and S. W. Huang, "Effects of plasma power and reaction gases on the surface properties of ePTFE materials during a plasma modification process," Surf. Coatings Technol., vol. 228, no. SUPPL.1, pp. S477-S481, 2013.

[38] A. Tan, D. Goh, Y. Farhatnia, N. G, J. Lim, S. H. Teoh, J. Rajadas, M. S. Alavijeh, and A. M. Seifalian, "An Anti-CD34 Antibody-Functionalized Clinical-Grade POSS-PCU Nanocomposite Polymer for Cardiovascular Stent Coating Applications: A Preliminary Assessment of Endothelial Progenitor Cell Capture and Hemocompatibility," PLoS One, vol. 8, no. 10, pp. 1-14, 2013.

[39] Q. L. Li, N. Huang, C. Chen, J. L. Chen, K. Q. Xiong, J. Y. Chen, T. X. You, J. Jin, and X. Liang, "Oriented immobilization of anti-CD34 antibody on titanium surface for self-endothelialization induction," J. Biomed. Mater. Res.—Part A, vol. 94, no. 4, pp. 1283-1293, 2010.

[40] F. Yang, S.-C. Feng, X.-J. Pang, W.-X. Li, Y.-H. Bi, Q. Zhao, S.-X. Zhang, Y. Wang, and B. Feng, "Combination coating of chitosan and anti-CD34 antibody applied on sirolimus-eluting stents can promote endothelialization while reducing neointimal formation," BMC Cardiovasc. Disord., vol. 12, no. 1, p. 96, 2012.

[41] M. Yin, Y. Yuan, C. Liu, and J. Wang, "Combinatorial coating of adhesive polypeptide and anti-CD34 antibody for improved endothelial cell adhesion and proliferation," J. Mater. Sci. Mater. Med., vol. 20, no. 7, pp. 1513-1523, 2009.

[42] J. Aoki, P. W. Serruys, H. Van Beusekom, A. T. L. Ong, E. P. McFadden, G. Sianos, W. J. Van Der Giessen, E. Regar, P. J. De Feyter, H. R. Davis, S. Rowland, and M. J. B. Kutryk, "Endothelial progenitor cell capture by stents coated with antibody against CD34: The HEAL-ING-FIM (Healthy Endothelial Accelerated Lining Inhibits Neointimal Growth-First in Man) registry," J. Am. Coll. Cardiol., vol. 45, no. 10, pp. 1574-1579, 2005.

[43] L. Chen, H. He, M. Wang, X. Li, and H. Yin, "Surface Coating of Polytetrafluoroethylene with Extracellular Matrix and Anti-CD34 Antibodies Facilitates Endothelialization and Inhibits Platelet Adhesion Under Sheer Stress," Tissue Eng. Regen. Med., vol. 14, no. 4, pp. 359-370, 2017.

[44] J. Chen, J. Cao, J. Wang, M. F. Maitz, L. Guo, Y. Zhao, Q. Li, K. Xiong, and N. Huang, "Biofunctionalization of titanium with PEG and anti-CD34 for hemocompatibility and stimulated endothelialization," J. Colloid Interface Sci., vol. 368, no. 1, pp. 636-647, 2012.

[45] R. R. Ravindranath, A. Romaschin, and M. Thompson, "In vitro and in vivo cell-capture strategies using cardiac stent technology—A review," Clin. Biochem., vol. 49, no. 1, pp. 186-191, 2016.

The invention claimed is:

1. A method for producing biofunctional fluorosilinated substrates comprising
   a. coating a surface of a substrate with a fluorosilane to create at least one fluorosilane monolayer on the surface to provide a fluorosilinated surface on the substrate wherein the substrate comprises surface hydroxyl groups or has been treated to form surface hydroxyl groups;
   b. plasma etching the fluorosilinated surface on the substrate to provide reactive functional groups on at least a portion of the fluorosilinated surface of the substrate; and
   c. attaching biospecies to the reactive functional groups to obtain the biofunctional fluorosilinated substrates,
   wherein the plasma etching in b is for about 10 seconds to about 1 minute and reduces the atomic percentage of fluorine on the substrate by no more than 10% as determined using xray photoelectron spectroscopy (XPS).

2. The method of claim 1, wherein the fluorosilane is selected from a compound of the Formula I:

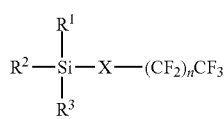

wherein
   X is a single bond or is $C_{1-6}$alkylene;
   n is an integer of from 0 to 12; and
   $R^1$, $R^2$ and $R^3$ are each independently a hydrolysable group.

3. The method of claim 1, further comprising coating the biofunctional fluorosilinated surface with a fluorinated lubricant following attachment of the biomolecule.

4. The method of claim 3, wherein the fluorinated lubricant is a perfluorocarbon oil selected from a perfluorotrialkylamine (e.g. a $C_{3-7}$perfluorotrialkylamine such as perfluorotripentylamine), a perfluoroalkylether or perfluoroalkylpolyether (e.g. a polymer of polyhexafluoropropylene oxide of the formula F—(CF(CF$_3$)—CF$_2$—O)$_m$—CF$_2$CF$_3$, wherein m is an integer of from 10 to 60), a perfluoroalkane (e.g. a $C_{5-12}$perfluoroalkane such as perfluorohexane or perfluorooctane), a perfluorocycloalkane (e.g. perfluorodecalin or perfluororperhydrophenanthrene) or a perfluorohaloalkane, wherein halo is other than fluoro (e.g. a $C_{5-12}$perfluorobromoalkane such as bromoperfluorooctane).

5. The method of claim 1, wherein the substrate is treated to form hydroxyl groups on a surface of the substrate using oxygen plasma and/or using a chemical treatment.

6. The method of claim 1, wherein the plasma etching is performed by oxygen, air, carbon dioxide, argon or nitrogen plasma.

7. The method of claim 6, wherein the plasma etching is performed by carbon dioxide plasma which forms both carboxyl ($CO_2H$) and hydroxyl (OH) groups on the substrate surface.

8. The method of claim 7, wherein the biospecies are covalently attached to carboxyl groups on the fluorosilinated surface via an amine-carboxyl reaction.

9. The method of claim 1, wherein the biospecies are selected from biomolecules, viruses, bacteria and cells.

10. The method of claim 9, wherein the biomolecules are selected from proteins, peptides, oligonucleotides, enzymes, and combinations thereof.

11. The method of claim 1, wherein the biospecies are attached to the reactive functional groups using coupling agents.

12. The method of claim 11, wherein the coupling agents are selected from one or more silanes selected from compounds of Formula II:

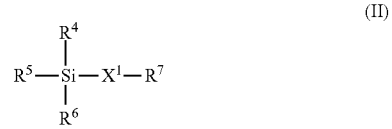

wherein
   one or more of $R^4$, $R^5$ and $R^6$ is OH or a group that is converted by hydrolysis to OH, and the remaining of $R^4$, $R^5$ and $R^6$ is selected from $C_{1-6}$alkyl;
   $X^1$ is linker; and
   $R^7$ is a reactive functional group that reacts with a complementary functional group on a biospecies to form a covalent bond.

13. The method of claim 12, wherein:
   the group that is converted by hydrolysis to OH is halo or —O—$C_{1-4}$alkyl;
   $X^1$ is $C_1$-$C_{20}$alkylene, $C_2$-$C_{20}$alkenylene or $C_2$-$C_{20}$alkynylene, each of which is optionally interrupted by O or C(O); and
   $R^7$ is an amino group, an epoxide, a glycidoxy group ( 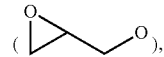 ), ($CO_2H$), an aldehyde (COH), an ester ($CO_2R^b$, wherein $R^b$ is $C_{1-6}$alkyl, benzyl, etc.), a tosyl group, halo or isocyanato (NCO).

14. The method of claim 1, wherein the biospecies is functionalized to allow them to covalently attach directly to the reactive functional groups on the substrate surface.

15. The method of claim 14, wherein prior to attaching the biospecies to the substrate's surface, carboxyl groups (COOH) present on the biospecies are modified with an amino-based coupling agent.

16. The method of claim 15, wherein the amino-based coupling agent is 3-aminopropyl-triethoxysilane (APTES).

17. The method of claim 14, wherein prior to attaching the biospecies to the substrate's surface, amino groups ($NH_2$) present on the biospecies are modified with an epoxy-based silane coupling agent.

18. The method of claim 17, wherein the epoxy-based silane coupling agent is (3-glycidyloxypropyl) trimethoxysilane.

19. The method of claim 1, wherein the biospecies is patterned on the substrates using both non-contact printing and contact printing, for example using conventional liquid phase deposition, droplet-dispensing non-contact printing, microcontact printing or contact printing.

* * * * *

UNITED STATES PATENT AND TRADEMARK OFFICE
CERTIFICATE OF CORRECTION

PATENT NO. : 12,343,452 B2
APPLICATION NO. : 16/960649
DATED : July 1, 2025
INVENTOR(S) : Tohid F. Didar et al.

Page 1 of 1

It is certified that error appears in the above-identified patent and that said Letters Patent is hereby corrected as shown below:

In the Claims

At Claim 1, Column 37, Line 16: "wherein the plasma etching in b is for about 10 seconds" should read --wherein the plasma etching in b. is for about 10 seconds--.

At Claim 13, Column 38, Line 40: "(CO2H), an aldehyde (COH), an ester (CO2Rb, wherein Rb" should read --a carboxylic acid (CO2H), an aldehyde (COH), an ester (CO2Rb, wherein Rb--.

Signed and Sealed this
Thirteenth Day of January, 2026

John A. Squires
*Director of the United States Patent and Trademark Office*